US010190982B2

(12) United States Patent
Kishima

(10) Patent No.: US 10,190,982 B2
(45) Date of Patent: Jan. 29, 2019

(54) INFORMATION PROCESSING DEVICE, IMAGE ACQUISITION SYSTEM, INFORMATION PROCESSING METHOD, IMAGE INFORMATION ACQUISITION METHOD, AND PROGRAM

(71) Applicant: SONY CORPORATION, Tokyo (JP)

(72) Inventor: Koichiro Kishima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/529,790

(22) PCT Filed: Sep. 30, 2015

(86) PCT No.: PCT/JP2015/077855
§ 371 (c)(1),
(2) Date: May 25, 2017

(87) PCT Pub. No.: WO2016/092940
PCT Pub. Date: Jun. 16, 2016

(65) Prior Publication Data
US 2017/0315056 A1    Nov. 2, 2017

(30) Foreign Application Priority Data

Dec. 8, 2014  (JP) ................................ 2014-248009

(51) Int. Cl.
*G01N 21/64* (2006.01)
*G02B 21/06* (2006.01)
(Continued)

(52) U.S. Cl.
CPC .............. *G01N 21/64* (2013.01); *A61B 1/00* (2013.01); *A61B 5/0071* (2013.01); *G01J 1/58* (2013.01);
(Continued)

(58) Field of Classification Search
CPC ...... G01N 21/64; G01N 21/6456; G02B 21/06
See application file for complete search history.

(56) References Cited

U.S. PATENT DOCUMENTS 5,239,375 A  8/1993 Mizoguchi et al.
5,257,100 A  10/1993 Hattori et al.
(Continued)

FOREIGN PATENT DOCUMENTS

CN  103153174 A  6/2013
DE  4204290 A1  5/1993
(Continued)

OTHER PUBLICATIONS

International Search Report and Written Opinion of PCT Application No. PCT/JP2015/077855, dated Dec. 22, 2015, 02 pages of English Translation and 07 pages of ISRWO.

*Primary Examiner* — Michael C Bryant
(74) *Attorney, Agent, or Firm* — Chip Law Group

(57) ABSTRACT

[Object] To propose an information processing device, an image acquisition system, an information processing method, an image information acquisition method, and a program which enable a position of a surface of a measurement subject to be more simply specified.
[Solution] An information processing device according to the present invention includes: a representative luminance value specifying unit configured to, when luminance values constituting a plurality of fluorescence images of a measurement subject captured while a position of the measurement subject in a thickness direction is changed are sequentially rearranged from a highest luminance value on the basis of the fluorescence images for each of the fluorescence images corresponding to respective thickness positions, extract a luminance value ranked at a predetermined position from the highest luminance value and set the extracted luminance value as a representative luminance value of the fluores-
(Continued)

cence image at the thickness position to be noted; and a surface position specifying unit configured to use the representative luminance value for each of the fluorescence images and set the thickness position corresponding to the fluorescence image that gives the maximum representative luminance value as a position corresponding to a surface of the measurement subject.

9 Claims, 21 Drawing Sheets

(51) Int. Cl.
    *A61B 1/00*     (2006.01)
    *G02B 21/36*     (2006.01)
    *A61B 5/00*     (2006.01)
    *G01J 1/58*     (2006.01)
    *G02B 21/16*     (2006.01)

(52) U.S. Cl.
    CPC .............. *G02B 21/06* (2013.01); *G02B 21/16* (2013.01); *G02B 21/36* (2013.01)

(56) References Cited

U.S. PATENT DOCUMENTS

| | | |
|---|---|---|
| 8,958,146 B2 | 2/2015 | Hattori et al. |
| 2003/0184730 A1 | 10/2003 | Price |
| 2004/0051051 A1* | 3/2004 | Kato .................. G01N 21/6402 250/458.1 |
| 2009/0147999 A1* | 6/2009 | Maeda ............... A61B 1/00009 382/106 |
| 2010/0317923 A1 | 12/2010 | Endo et al. |
| 2012/0314206 A1 | 12/2012 | Spizig et al. |
| 2013/0204134 A1 | 8/2013 | Harks et al. |

FOREIGN PATENT DOCUMENTS

| | | |
|---|---|---|
| DE | 202010010932 U1 | 10/2011 |
| EP | 2070469 A1 | 6/2009 |
| EP | 2266453 A1 | 12/2010 |
| EP | 2503373 A | 9/2012 |
| EP | 2561392 A1 | 2/2013 |
| EP | 2627241 A1 | 8/2013 |
| JP | 4-138127 A | 5/1992 |
| JP | 5-128251 A | 5/1993 |
| JP | 11-108615 A | 4/1999 |
| JP | 2009-160386 A | 7/2009 |
| JP | 2010-284369 A | 12/2010 |
| JP | 2012-203048 A | 10/2012 |
| JP | 2013-011527 A | 1/2013 |
| JP | 2013-525838 A | 6/2013 |
| JP | 2013-544551 A | 12/2013 |
| RU | 2013121803 A | 11/2014 |
| WO | 2011/131311 A1 | 10/2011 |
| WO | 2012/049621 A1 | 4/2012 |

* cited by examiner

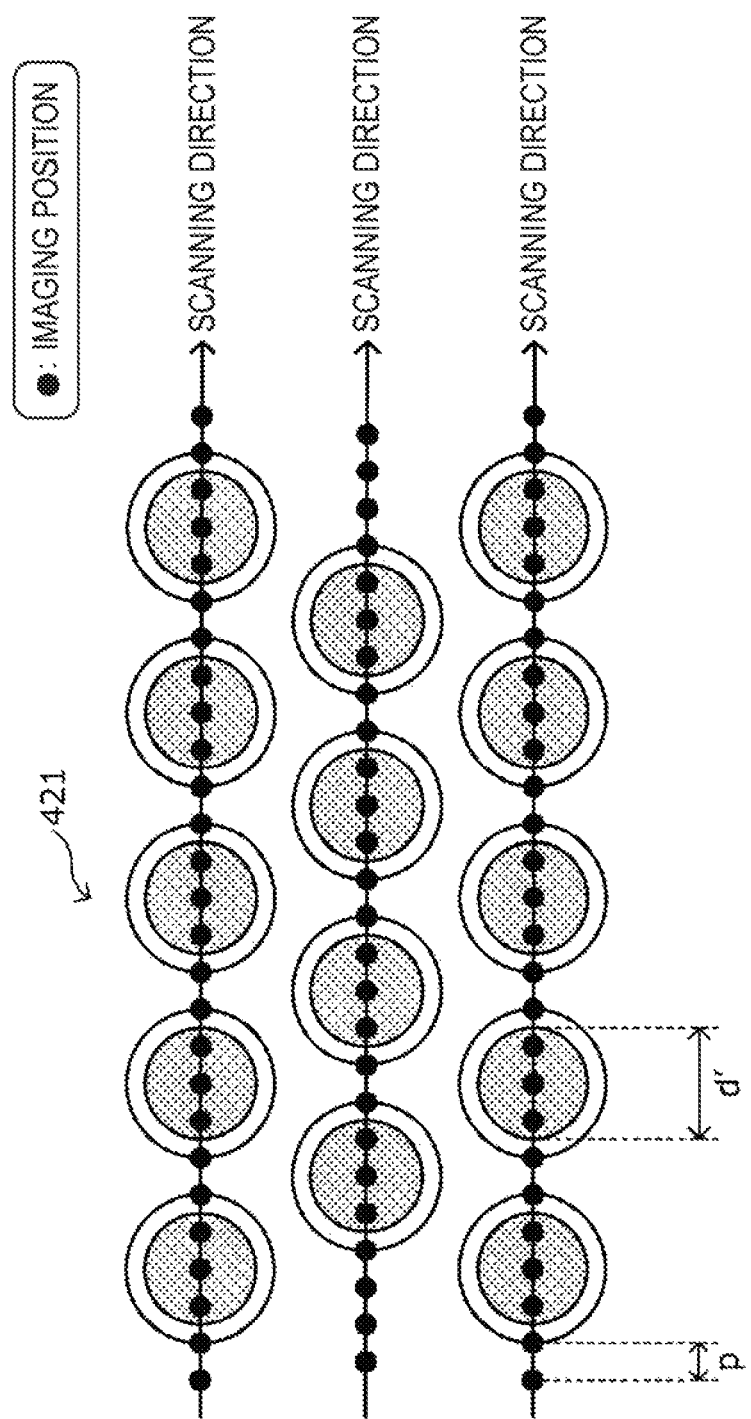

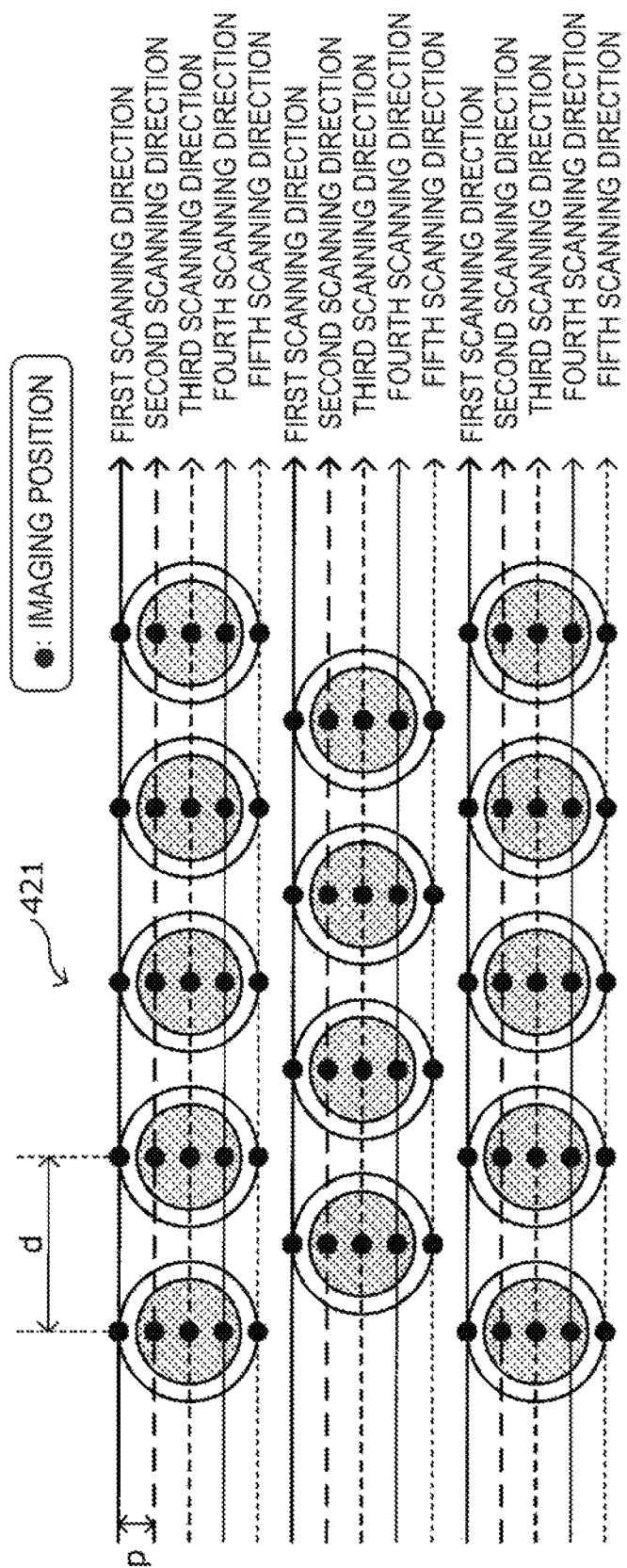

INFORMATION PROCESSING DEVICE, IMAGE ACQUISITION SYSTEM, INFORMATION PROCESSING METHOD, IMAGE INFORMATION ACQUISITION METHOD, AND PROGRAM

CROSS REFERENCE TO RELATED APPLICATIONS

This application is a U.S. National Phase of International Patent Application No. PCT/JP2015/077855 filed on Sep. 30, 2015, which claims priority benefit of Japanese Patent Application No. JP 2014-248009 filed in the Japan Patent Office on Dec. 8, 2014. Each of the above-referenced applications is hereby incorporated herein by reference in its entirety.

TECHNICAL FIELD

The present disclosure relates to an information processing device, an image acquisition system, an information processing method, an image information acquisition method, and a program.

BACKGROUND ART

A laser confocal microscope disclosed below in Patent Literature 1, for example, has been proposed as a laser confocal microscope (a microendoscope) which uses an image guide fiber composed of a plurality of optical fiber element wires. A microendoscope system proposed in Patent Literature 1, for example, transmits fluorescence generated by exciting an observation target with one photon through an image guide fiber and enables the generated fluorescence to be observed.

When an image captured by such a fluorescence observation system (i.e., a fluorescence image) is observed, it is important to specify where a position of a surface or a position of a focus of an observation target is. Non-Patent Literature 1 described below discloses a method for specifying a position of a surface or a position of a focus of an observation target by applying an image recognition technology to a fluorescence image obtained using a field-of-view (FOV) type fluorescence microscope.

CITATION LIST

Patent Literature

Patent Literature 1: JP 2007-530197T

Non-Patent Literature

Non-Patent Literature 1: K. Kishima, "Simple way of pinpointing the three-dimensional position of biomarkers in fluorescence microscopy using a through-focus exposure method," APPLIED OPTICS, 2011, Vol. 50, No. 25, p. 4989

Non-Patent Literature 2: J. Rosen and G. Brooker, "Nonscanning motionless fluorescence three-dimensional holographic microscopy," Nat. Photonics 2, 190-195 (2008)

Non-Patent Literature 3: C. Maurer, S. Khan, S. Fassl, S. Bernet, and M. Ritsch-Marte, "Depth of field multiplexing in microscopy," Opt. Express 18, 3023-3033 (2010)

Non-Patent Literature 4: P. A. Dalgarno, H. I. C. Dalgarno, A. Putoud, R. Lambert, L. Paterson, D. C. Logan, D. P. Towers, R. J. Warburton, and A. H. Greenaway, "Multiplane imaging and three dimensional nanoscale particle tracking in biological microscopy," Opt. Express 18, 877-883 (2010)

DISCLOSURE OF INVENTION

Technical Problem

Here, the method disclosed in Non-Patent Literature 1 is a technology of applying an image recognition process to a fluorescence image obtained using a specific fluorescence microscope. Thus, it is extremely difficult to apply the method disclosed in the above-described Non-Patent Literature 1 to an object having a bright spot with an unclear size in a fluorescence image, like in a multi-photon fluorescence image obtained using a multi-photon fluorescence microscope.

Thus, a method in which a position of a surface of a measurement subject can be more simply specified regardless of an excitation process to generate fluorescence or a type of a fluorescence microscope used in fluorescence measurement has been desired.

Therefore, the present disclosure takes the above circumstances into consideration and proposes an information processing device, an image acquisition system, an information processing method, an image information acquisition method, and a program which enable a position of a surface of a measurement subject to be more simply specified with respect to an arbitrary fluorescence image.

Solution to Problem

According to the present disclosure, there is provided an information processing device including: a representative luminance value specifying unit configured to, when luminance values constituting a plurality of fluorescence images of a measurement subject captured while a position of the measurement subject in a thickness direction is changed are sequentially rearranged from a highest luminance value on the basis of the fluorescence images for each of the fluorescence images corresponding to respective thickness positions, extract a luminance value ranked at a predetermined position from the highest luminance value and set the extracted luminance value as a representative luminance value of the fluorescence image at the thickness position to be noted; and a surface position specifying unit configured to use the representative luminance value for each of the fluorescence images and set the thickness position corresponding to the fluorescence image that gives the maximum representative luminance value as a position corresponding to a surface of the measurement subject.

Further, according to the present disclosure, there is provided an image acquisition system including: an imaging unit configured to generate a plurality of pieces of image data for fluorescence generated from a measurement subject by radiating excitation light toward the measurement subject and imaging the fluorescence of the measurement subject while changing a position of the measurement subject in a thickness direction; and an arithmetic processing unit configured to generate a plurality of fluorescence images corresponding to respective thickness positions by controlling the imaging unit and performing data processing on each of the plurality of pieces of image data generated by the imaging unit. The imaging unit includes a light source optical system configured to guide excitation light for exciting the measurement subject with two or more photons to generate fluorescence toward the measurement subject, an image guide fiber which is formed by bundling a plurality of multimode optical fiber element wires and is configured to transmit the excitation light incident on one end to the measurement subject from the light source optical system and transmit an image of the measurement subject formed on the other end using the fluorescence generated from the measurement subject to the one end, and an imaging optical system configured to scan the image of the measurement subject transmitted to the one end of the image guide fiber at a scanning pitch that is narrower than a size of a core of each of the plurality of optical fiber element wires to perform imaging such that at least a part of an optical fiber element wire-corresponding area which corresponds to each of the optical fiber element wires is included in a plurality of images, and generate a plurality of pieces of image data of the measurement subject. The arithmetic processing unit includes a selection unit configured to select, for each of a plurality of pixels constituting the optical fiber element wire-corresponding area, a pixel value that has maximum luminance among the plurality of pieces of image data as a representative pixel value of the pixel, a captured image re-constructing unit configured to re-construct the captured image of the measurement subject using the selected representative pixel value and generate the fluorescence image, a representative luminance value specifying unit configured to, when luminance values constituting the plurality of fluorescence images captured while the position of the measurement subject in the thickness direction is changed are sequentially rearranged from a highest luminance value on the basis of the fluorescence images for each of the fluorescence images corresponding to respective thickness positions, extract a luminance value ranked at a predetermined position from the highest luminance value and set the extracted luminance value as a representative luminance value of the fluorescence image at the thickness position to be noted, and a surface position specifying unit configured to use the representative luminance value for each of the fluorescence images and set the thickness position corresponding to the fluorescence image that gives the maximum representative luminance value as a position corresponding to a surface of the measurement subject.

Further, according to the present disclosure, there is provided an information processing method including: extracting, when luminance values constituting a plurality of fluorescence images of a measurement subject captured while a position of the measurement subject in a thickness direction is changed are sequentially rearranged from a highest luminance value on the basis of the fluorescence images for each of the fluorescence images corresponding to respective thickness positions, a luminance value ranked at a predetermined position from the highest luminance value and setting the extracted luminance value as a representative luminance value of the fluorescence image to be noted; and using the representative luminance value for each of the fluorescence images and setting the thickness position corresponding to the fluorescence image that gives the maximum representative luminance value as a position corresponding to a surface of the measurement subject.

Further, according to the present disclosure, there is provided an image information acquisition method including: guiding excitation light for exciting a measurement subject with two or more photons to generate fluorescence toward the measurement subject; transmitting the excitation light incident on one end of an image guide fiber which is formed by bundling a plurality of multimode optical fiber element wires toward the measurement subject using the image guide fiber, and transmitting an image of the measurement subject formed on the other end using the fluorescence generated from the measurement subject to the one end while changing a position of the measurement subject in a thickness direction; scanning the image of the measurement subject transmitted to the one end of the image guide fiber at a scanning pitch that is narrower than a size of a core of each of the plurality of optical fiber element wires to perform imaging such that at least a part of an optical fiber element wire-corresponding area which corresponds to each of the optical fiber element wires is included in a plurality of images, and generating a plurality of pieces of image data of the measurement subject; selecting, for each of a plurality of pixels constituting the optical fiber element wire-corresponding area, a pixel value that has maximum luminance among the plurality of pieces of image data as a representative pixel value of the pixel; re-constructing the captured image of the measurement subject using the selected representative pixel value and generating the fluorescence image; extracting, when luminance values constituting a plurality of fluorescence images captured while the position of the measurement subject in the thickness direction is changed are sequentially rearranged from a highest luminance value on the basis of the fluorescence images for each of the fluorescence images corresponding to respective thickness positions, a luminance value ranked at a predetermined position from the highest luminance value and setting the extracted luminance value as a representative luminance value of the fluorescence image at the thickness position to be noted; and using the representative luminance value for each of the fluorescence images and setting the thickness position corresponding to the fluorescence image that gives the maximum representative luminance value as a position corresponding to a surface of the measurement subject.

Further, according to the present disclosure, there is provided a program causing a computer to realize: a representative luminance value specifying function of extracting, when luminance values constituting a plurality of fluorescence images of a measurement subject captured while a position of the measurement subject in a thickness direction is changed are sequentially rearranged from a highest luminance value on the basis of the fluorescence images for each of the fluorescence images corresponding to thickness positions, a luminance value ranked at a predetermined position from the highest luminance value and setting the extracted luminance value as a representative luminance value of the fluorescence image to be noted; and a surface position specifying function of using the representative luminance value for each of the fluorescence images and setting the thickness position corresponding to the fluorescence image that gives the maximum representative luminance value as a position corresponding to a surface of the measurement subject.

According to the present disclosure, using a plurality of fluorescence images captured while a position of a measurement subject in a thickness direction is changed, representative luminance values of the fluorescence images corresponding to thickness positions are specified, and a thickness position corresponding to a fluorescence image that gives a maximum representative luminance value is set as a position corresponding to a surface of the measurement subject.

Advantageous Effects of Invention

According to the above-described present disclosure, a position of a surface of a measurement subject can be more simply specified with respect to an arbitrary fluorescence image.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 16A is an illustrative diagram schematically showing a scanning method of the image guide fiber of the imaging unit according to the embodiment.

FIG. 16B is an illustrative diagram schematically showing a scanning method of the image guide fiber of the imaging unit according to the embodiment.

MODE(S) FOR CARRYING OUT THE INVENTION

Figure 1:
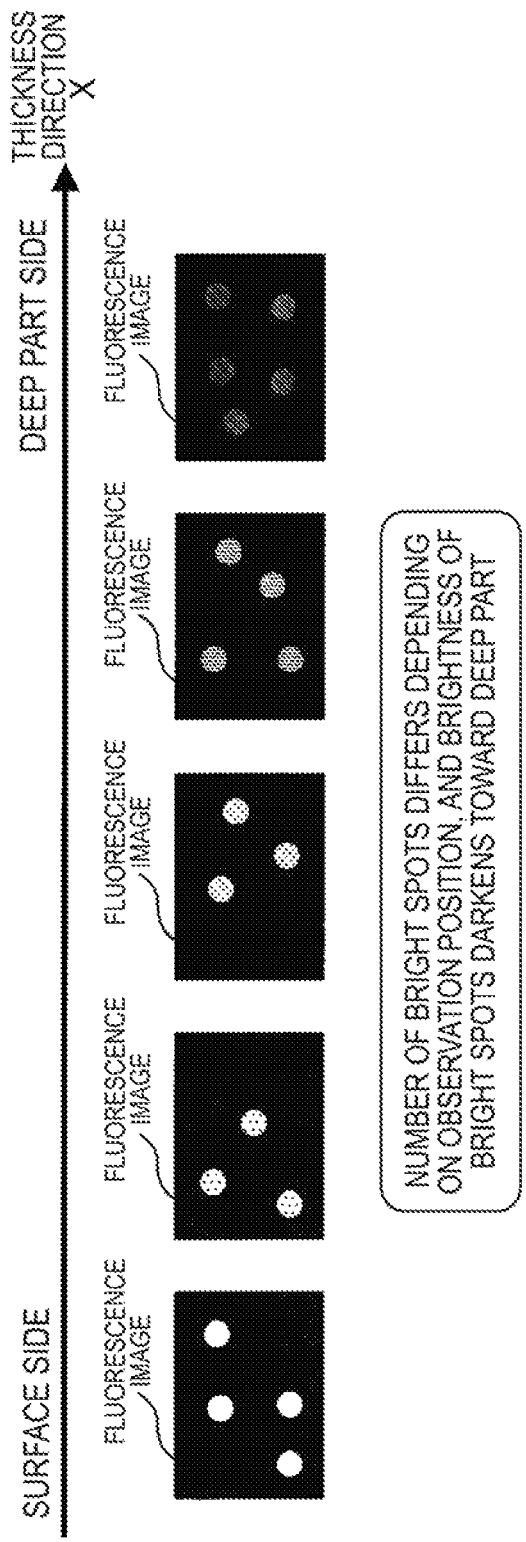
FIG. 1 is an illustrative diagram for describing fluorescence images.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that description will be provided in the following order.
1. Regarding fluorescence image
2. First embodiment (Information processing device)
3. Second embodiment (Image acquisition system)
(Regarding Fluorescence Image)

Before an information processing device and an image acquisition system according to an embodiment of the present disclosure are described, a fluorescence image to be noted in the present disclosure will be briefly described.

As endoscope technologies have developed in recent years, surgical operations or intraoperative diagnoses have been conducted under endoscopes. Here, when it is determined whether a cell to be noted is a normal cell or a cancer cell, a predetermined fluorescent dye is injected into an organ to be noted, and then a fluorescence image of the organ is observed using a fluorescence microscope connected to an endoscope.

Here, when a specimen (a measurement subject) having a three-dimensional structure is observed using a fluorescence microscope, as with observation of a three-dimensionally cultured cell as well as the above-described in-vivo somatoscopy, it is more difficult to determine which position is a surface in comparison to a case of bright field observation.

It is not obvious in a fluorescence image which bright spot observed in the image is present at a position close to a surface (a position close to an object lens). For this reason, a user compares positions at which bright spots have a high contrast or positions at which contours of bright spots are apparent to each other for each bright spot, selects a bright spot focused at a position closest to the object lens among the bright spots, and then specifies a position of a surface of a cell.

When a measurement subject is fluorescent beads having a uniform diameter that is uniform and smaller than a focal depth, anyone can specify a position of a surface even though he or she is not a skilled person. However, when a substance having a variable shape and a variety of thicknesses, like cells or the like, is a measurement subject, it is not possible to specify a position of a surface thereof unless a three-dimensional structure of the measurement subject can be imagined, and thus specification of a position of a surface of a measurement subject depends on user proficiency. For this reason, a method in which a position of a surface of a measurement subject can be simply specified in a fluorescence image without relying on user proficiency has been desired.

Applying the image recognition technology as described in Non-Patent Literature 1 is considered in order to, for example, specify a position of a surface of a measurement subject in a fluorescence image. However, as described above, the technology of Non-Patent Literature 1 is a technology applicable to a fluorescence image obtained using a specific fluorescence microscope, and using the technology entails difficulty. In addition, use of an auto-focus technology for detecting a position of slide glass is also considered, however, the technology is not applied under an environment in which no slide glass is used as in in-vivo somatoscopy.

Therefore, the inventor focused on using some kind of information that can be obtained from a fluorescence image to specify a position of a surface regardless of the use of a fluorescence microscope or a fluorescence excitement process. One kind of information considered as the information is an average luminance value of fluorescence images.

Figure 2:
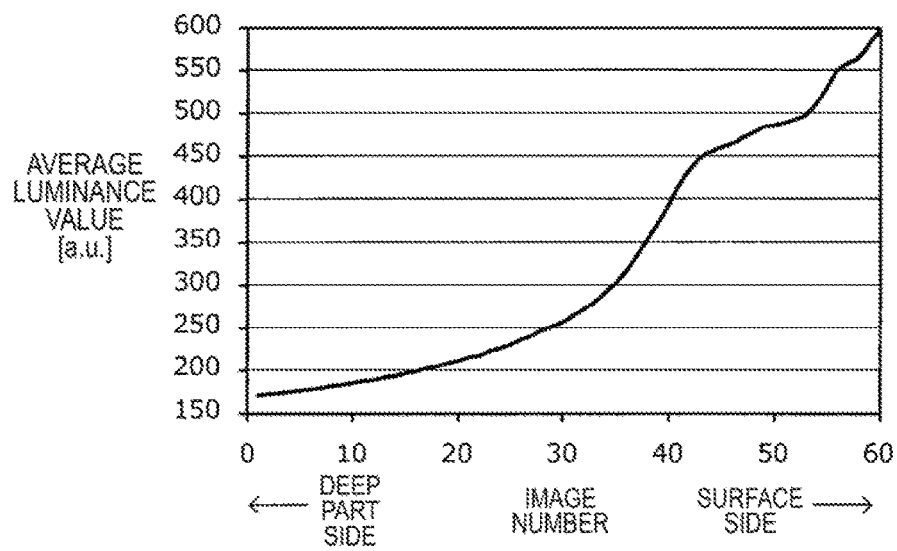
FIG. 2 is a graph diagram for describing the fluorescence images.

FIG. 1 is an illustrative diagram for describing fluorescence images, and FIG. 2 is a graph diagram for describing the fluorescence images.

With respect to the fluorescence images, brightness of bright spots generally brightens as the fluorescence images are observed on a side closer to a surface, and brightness of the bright spots darkens as the fluorescence images are observed on a side farther from the surface since a thickness that the fluorescence should permeate is increased, as schematically shown in FIG. 1. In addition, fluorescence images tend to be bright overall at observation positions at which the fluorescence images are out of focus. In addition, the number of bright spots differs depending on observation positions of a measurement subject in a thickness direction (a depth direction) as schematically shown in FIG. 1.

FIG. 2 is a diagram in which a change in average luminance values of the fluorescence images when fluorescence that is generated by a certain cell is observed from a deep part side of the cell to a surface side with an interval of 5 μm is plotted. In FIG. 2, the horizontal axis represents numbers (image numbers) associated with the fluorescence images sequentially captured from the deep part side, and the vertical axis represents the average luminance values.

As can be seen from FIG. 2, when an average luminance value of a fluorescence image to be noted is employed as one kind of information obtained from luminance values of the fluorescence images, the average luminance value increases toward the surface side of a measurement subject. For this reason, it is not possible to specify a position of a surface of the measurement subject when attention is paid to the average luminance values.

As a result of further intense examination on the basis of the above-described knowledge, the present inventor has decided to focus on a distribution of luminance values itself, rather than an average luminance value of fluorescence images, and has completed an information processing device and an image acquisition system according to an embodiment of the present disclosure to be described in detail below.

First Embodiment

Figure 3:
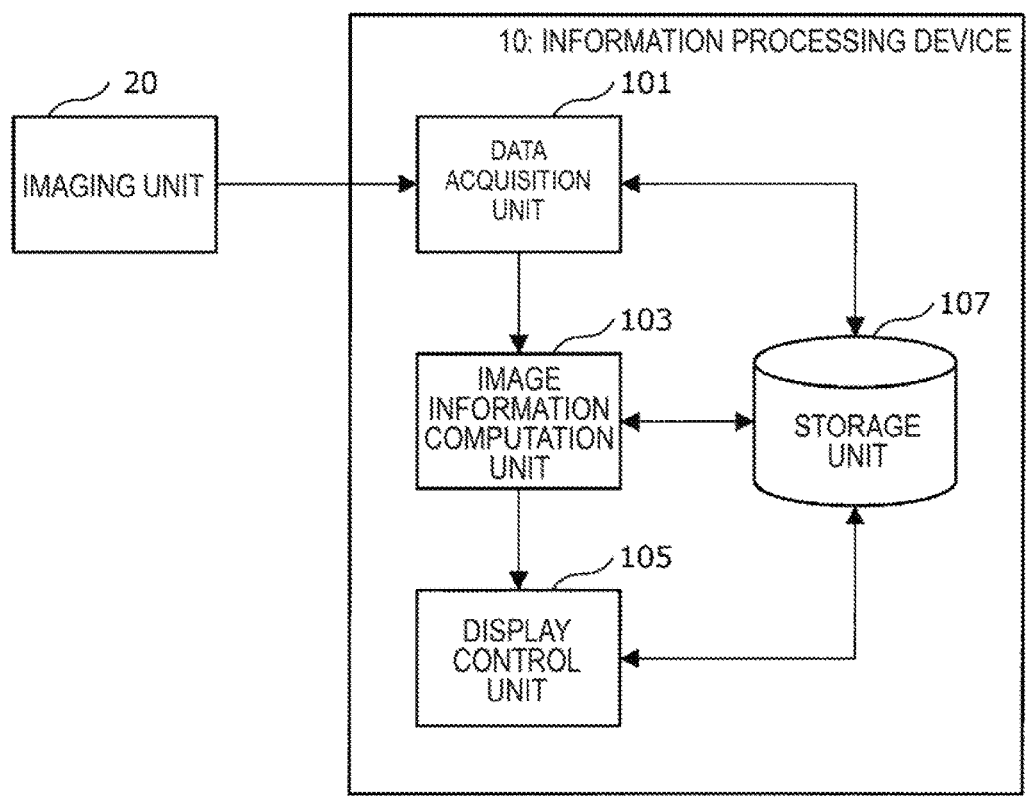
FIG. 3 is a block diagram showing an example of a configuration of an information processing device according to a first embodiment of the present disclosure.
Figure 4:
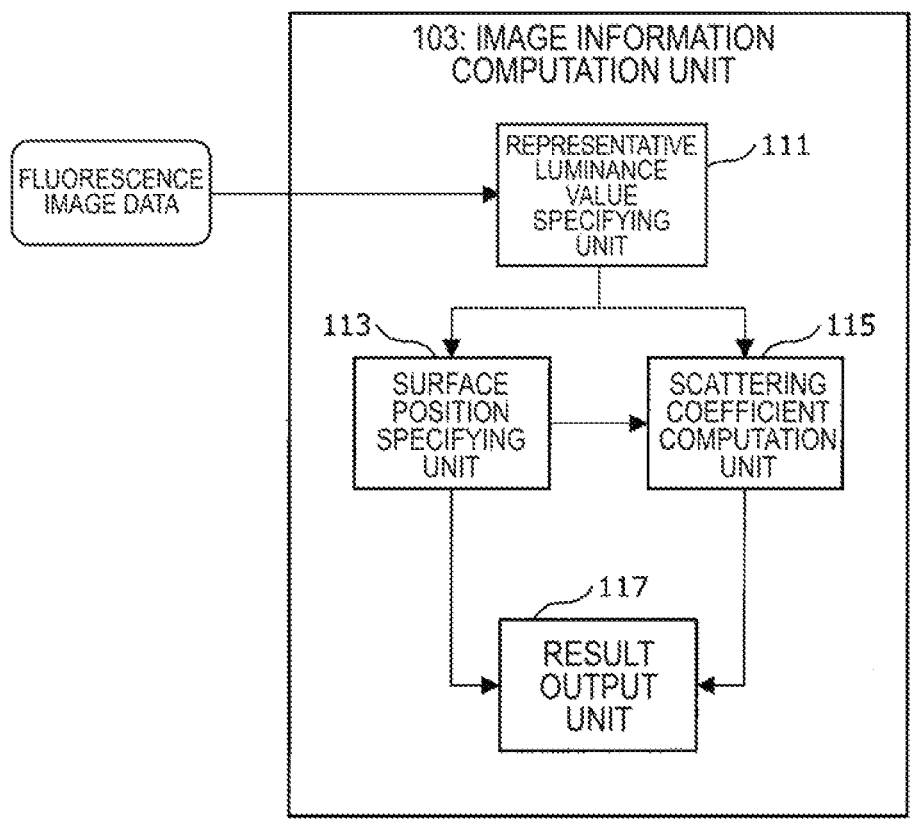
FIG. 4 is a block diagram showing an example of a configuration of an image information computation unit according to the embodiment.

An information processing device according to a first embodiment of the present disclosure will be described in detail below with reference to FIGS. 3 to 9. FIG. 3 is a block diagram showing an example of a configuration of the information processing device according to the present embodiment, and FIG. 4 is a block diagram showing an example of a configuration of an image information computation unit provided in the information processing device according to the present embodiment. FIGS. 5 to 9 are illustrative diagrams for describing an image information computation process according to the present embodiment.

<Overall Configuration of Information Processing Device>

First, an overall configuration of an information processing device 10 according to the present embodiment will be described with reference to FIG. 3.

The information processing device 10 according to the present embodiment is a device which acquires a fluorescence image of a measurement subject captured by an imaging unit 20, uses the fluorescence image, and computes image information relevant to the fluorescence image including at least a position of a surface of the measurement subject.

The information processing device 10 may be an information processing device such as any of a variety of computers and servers provided outside the imaging unit 20, or may be an arithmetic operation chip constituted by a central processing unit (CPU), a read only memory (ROM), a random access memory (RAM), and the like installed in the imaging unit 20.

Here, a measurement subject is not particularly limited as long as it is a substance that emits fluorescence, and the measurement subject may be an inanimate object such as a fluorescence bead or an animate object such as any of a variety of kinds of cells. In addition, fluorescence emitted from a measurement subject may be emitted by the measurement subject itself, or may be emitted by any of a variety of fluorescent dyes added to the measurement subject. Furthermore, there is no particular limit on an excitation process of such fluorescence, and it may be fluorescence emitted from a fluorescent substance excited in a one-photon process, or may be fluorescence emitted from a fluorescence substance excited in a multiple-photon processes, for example, a two-photon process.

In addition, the imaging unit 20 that captures such a fluorescence image is a unit which radiates excitation light having a predetermined wavelength toward a measurement subject, detects fluorescence generated from the measurement subject, and thereby generates image data regarding the generated fluorescence. Any device such as one of a variety of kinds of fluorescence microscopes can be used as the imaging unit 20 as long as the device can capture fluorescence images while changing a position of a measurement subject in the thickness direction.

The information processing device 10 according to the present embodiment mainly has a data acquisition unit 101, an image information computation unit 103, a display control unit 105, and a storage unit 107 as illustrated in FIG. 3.

The data acquisition unit 101 is realized by, for example, a CPU, a ROM, a RAM, a communication device, and the like. The data acquisition unit 101 acquires image data of a plurality of fluorescence images generated by the imaging unit 20 in which the measurement subject has a different thickness direction from the imaging unit 20. The image data of the plurality of fluorescence images acquired by the data acquisition unit 101 is transmitted to the image information computation unit 103 to be described below. In addition, the data acquisition unit 101 may associate the acquired image data of the plurality of fluorescence images with time information regarding a date, time, and the like on which the image data is acquired and store the associated data in the storage unit 107 to be described below as history information.

The image information computation unit 103 is realized by, for example, a CPU, a ROM, a RAM, and the like. The image information computation unit 103 computes image information including at least information regarding a position corresponding to a surface of the measurement subject using the plurality of fluorescence images transmitted from the data acquisition unit 101, in which the measurement subject has a different thickness direction. In addition, the image information computation unit 103 may also compute information regarding a scattering coefficient of the measurement subject as image information. When the image information mentioned above has been computed, the image information computation unit 103 outputs information regarding the computed image information to the display control unit 105. Accordingly, the image information regarding the fluorescence images of the measurement subject S is output to a display unit (not illustrated) provided in the information processing device 10 or any of various computers that can communicate with the information processing device 10. In addition, the image information computation unit 103 may output the obtained image information to any of a variety of recording media, computers, or the like, or to a paper medium using an output device such as a printer. In addition, the image information computation unit 103 may associate the image information regarding the fluorescence images of the measurement subject S with time information regarding a date, time, and the like at which the information was computed and store the associated data in the storage unit 107 or the like as history information.

Note that a detailed configuration of the image information computation unit 103 will be described below.

The display control unit 105 is realized by, for example, a CPU, a ROM, a RAM, an output device, and the like. The display control unit 105 performs display control to display a position of a surface of the measurement subject S or various processing results including the image information regarding the scattering coefficient of the measurement subject S or the like transmitted from the image information computation unit 103 on an output device such as a display of the information processing device 10 and an output device provided outside of the information processing device 10. Accordingly, a user of the information processing device 10 can immediately ascertain the various processing results with regard to the measurement subject S.

The storage unit 107 is realized by, for example, a RAM of the information processing device 10 according to the present embodiment, a storage device, or the like. The storage unit 107 appropriately records various parameters or process developments that need to be saved by the information processing device 10 according to the present embodiment to perform any process, or various databases, programs, and the like. The storage unit 107 enables the data acquisition unit 101, the image information computation unit 103, the display control unit 105, and the like to freely perform data read and write processes.

[Regarding Configuration of Image Information Computation Unit 103]

Next, a detailed configuration of the image information computation unit 103 of the information processing device 10 according to the present embodiment will be described with reference to FIGS. 4 to 9.

The image information computation unit 103 according to the present embodiment has, for example, a representative luminance value specifying unit 111, a surface position specifying unit 113, a scattering coefficient computation unit 115, and a result output unit 117 as illustrated in FIG. 4.

The representative luminance value specifying unit 111 is realized by, for example, a CPU, a ROM, a RAM, and the like. The representative luminance value specifying unit 111 executes, on the basis of the plurality of fluorescence images that were captured d while the position of the measurement subject S is changed in the thickness direction, a process (a sorting process) of sequentially rearranging luminance values constituting the plurality of fluorescence images from the highest luminance value for each of the fluorescence images corresponding to thickness positions thereof. Thereafter, the representative luminance value specifying unit 111 extracts a luminance value ranked at a predetermined position from the highest luminance value and sets the extracted luminance value as a representative luminance value of a fluorescence image at a thickness position to be noted.

Figure 5:
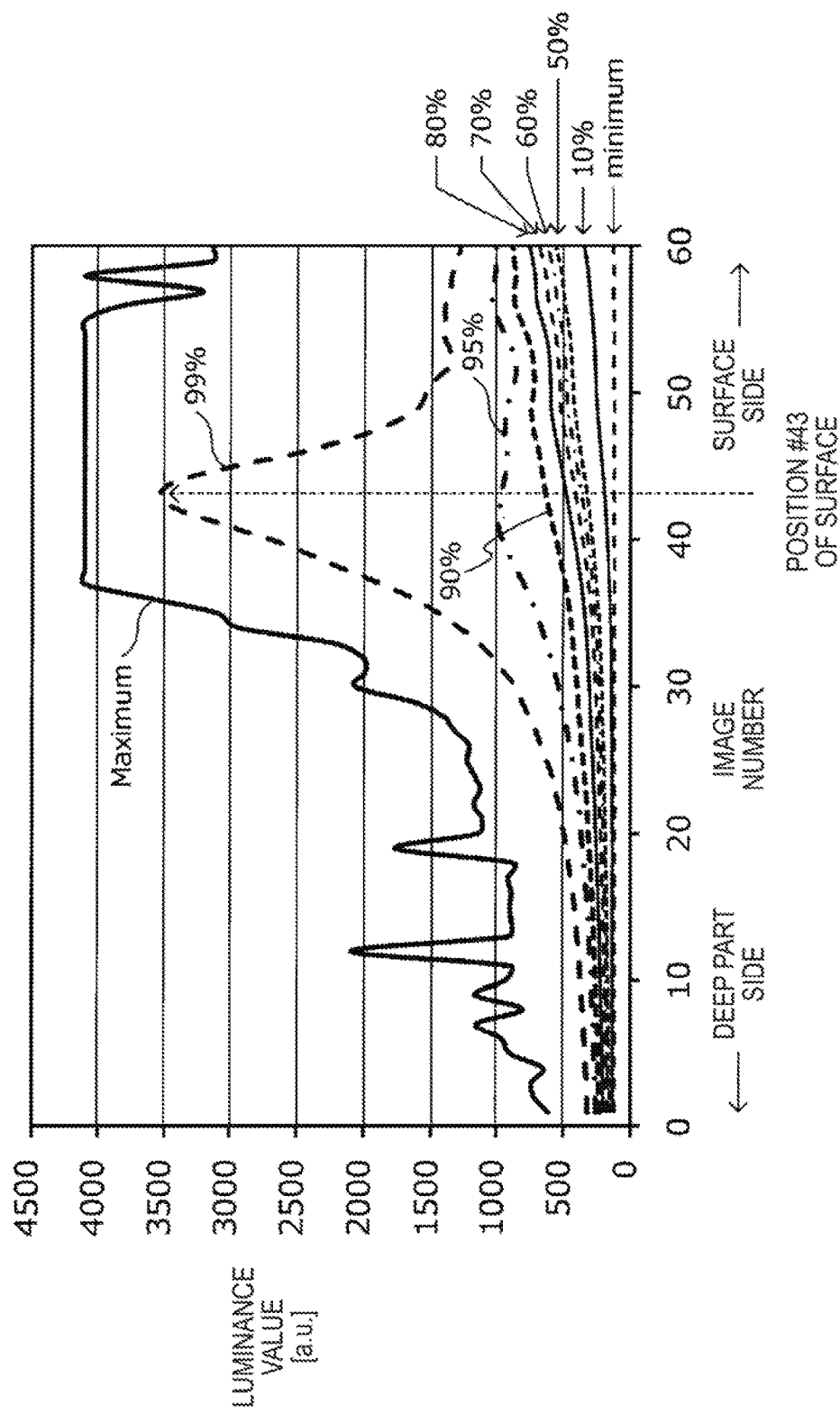
FIG. 5 is an illustrative diagram for describing an image information computation process according to the embodiment.

FIG. 5 shows results of a sorting process for luminance values performed using fluorescence images obtained by imaging fluorescence from eGFP generated from the measurement subject S (specifically, an eGFP-RFP expression cancer tissue cell created in an individual mouse: MKN 45 (a human gastric cancer epithelial cell)) while changing fluorescence by 5 μm in a depth direction. In FIG. 5, the horizontal axis represents numbers (image numbers: #1 to #60) linked to fluorescence images that are sequentially captured from the depth side, and a higher number denotes that the florescence image is approaching a surface side. In addition, the vertical axis represents luminance values.

If sequential sorting of luminance values of all pixels constituting one fluorescence image from the highest luminance value to the lowest luminance value is performed for each of the plurality of fluorescence images and then a change in the highest luminance values of the fluorescence images is plotted, a curve denoted as "Maximum" in FIG. 5 is obtained. Likewise, if luminance values ranked in the top 1% of the highest luminance values (for example, the $10,000^{th}$ luminance value from the top in case of data of a fluorescence image having one million pixels) are plotted, a curve denoted as "99%" in FIG. 5 is obtained. Likewise for other values in FIG. 5, changes of luminance values ranked in the top 5% ("95%" in the diagram), the top 10% ("90%" in the diagram), the above-described 20% ("80%" in the diagram), 30% ("70%" in the diagram), 40% ("60%" in the diagram), 50% ("50%" in the diagram), 90% ("10%" in the diagram), and a minimum pixel value ("minimum" in the diagram) are plotted.

Here, for the image information computation unit 103 according to the present embodiment, a "fluorescence image that is the brightest and in focus is considered to be a fluorescence image for a surface of the measurement subject S. Here, if the fluorescence images have a substantially equal probability of having bright spots, the same bright spots can be regarded as being observed when luminance values of all pixels of the fluorescence images are sequentially sorted from the highest luminance value. As illustrated in FIG. 5, if a curve exponentially changes when a change in the luminance values in accordance with a change in a thickness position is plotted, the above-described precondition can be determined to be substantially satisfied. Thus, if a plot of ranked positions at which luminance values exponentially change is specified by plotting the change in the luminance values at specific ranked positions of the fluorescence images having different depth directions and a position of a highest luminance value can be specified on the basis of the plot as illustrated in FIG. 5, a position of a surface of the measurement subject S can be decided.

Referring to the state of the luminance values corresponding to "Maximum" in FIG. 5, the change in the luminance values is not even, but there are several peaks in the number #1 to the number #30. The reason for this is considered to be that electric noise caused by a laser, an image sensor, or the like that is used to generate the fluorescence images has been superimposed. In addition, luminance values are saturated from the number #35.

In addition, referring to the state of the change in the luminance values ranked in the top 1% (the plot of "99%") in FIG. 5, a substantially exponential change in luminance values is found from the number #1 to the number #40. In addition, referring to the change in the luminance values ranked in the top 5% (the plot of (95%)), while an even change is found from the number #1 to the number #40, no exponential change in luminance values is found, unlike the plot of "99%." In addition, the change in the luminance values ranked in the top 10% or higher monotonously increases from the number #1 to the number #60, and thus the luminance values are not used to specify a position of a surface.

Thus, the representative luminance value specifying unit 111 can specify the position of the surface of the measurement subject S to be noted by dealing with the luminance values ranked in the top 1% (i.e., the luminance values on the plot of "99%" in FIG. 5) among the plots shown in FIG. 5 as representative luminance values.

Here, a rank from the top position at which luminance values to be noted are positioned may be appropriately selected in accordance with a density of bright spots of a fluorescence image to be noted, however, for example, a rank in the range of the top 0.5% to 5% of the number of all pixels constituting one fluorescence image with reference to a highest luminance value is preferable. A case of a rank in the top 0.5% or less is not preferable because there is a possibility of various kinds of electric noise being superimposed on the luminance values like the plot of "Maximum" in FIG. 5. In addition, a case of a rank exceeding the top 5% is not preferable because there is a possibility of luminance values increasing monotonously, like the plot of "90%" in FIG. 5.

The representative luminance value specifying unit 111 extracts a luminance value ranked at a predetermined position from the highest luminance value of each of fluorescence images as a representative luminance value.

The representative luminance value specifying unit 111 outputs information of the representative luminance value extracted as described above to the surface position specifying unit 113 and the scattering coefficient computation unit 115 to be described below.

The surface position specifying unit 113 is realized by, for example, a CPU, a ROM, a RAM, and the like. The surface position specifying unit 113 specifies a position corresponding to a surface of the measurement subject S on the basis of a representative luminance value of each fluorescence image extracted by the representative luminance value specifying unit 111. Specifically, the surface position specifying unit 113 sets a thickness position corresponding to a fluorescence image that gives a maximum representative luminance value among the representative luminance values of the respective fluorescence images as a position corresponding to the surface of the measurement subject S to be noted.

In the example shown in FIG. 5, for example, the plot of the luminance values denoted as "99%" in the diagram is set as a plot expressing a state of a change in representative luminance values, however, the surface position specifying unit 113 specifies a position of the number #43 (i.e., a position 5 μm×43=215 μm upward from a measurement start position), which is a position at which the maximum luminance value is given among the plots expressing the changes of the representative luminance values, as the position of the surface of the measurement subject S to be noted.

The surface position specifying unit 113 outputs information regarding the position of the surface of the measurement subject S specified as described above to the scattering coefficient computation unit 115 and the result output unit 117 to be described below.

The scattering coefficient computation unit 115 is realized by, for example, a CPU, a ROM, a RAM, and the like. The scattering coefficient computation unit 115 uses the representative luminance values of the respective fluorescence images and computes a scattering coefficient of the measurement subject from a degree of change in the representative luminance values in the thickness direction.

As described above, luminance values at the ranks extracted as the representative luminance values exponentially change in accordance with a change in the position in the thickness direction. Thus, by focusing on the change in the representative luminance values in the thickness direction, a scattering coefficient of the measurement subject S can be obtained from the degree of change.

In more detail, the scattering coefficient computation unit 115 computes a scattering coefficient using representative luminance values at three thickness positions having equal intervals on the basis of representative luminance values of fluorescence images corresponding to deeper parts than the position corresponding to the surface of the measurement subject S. A scattering coefficient computation process by the scattering coefficient computation unit 115 will be described in detail below with reference to FIG. 6.

Figure 6:
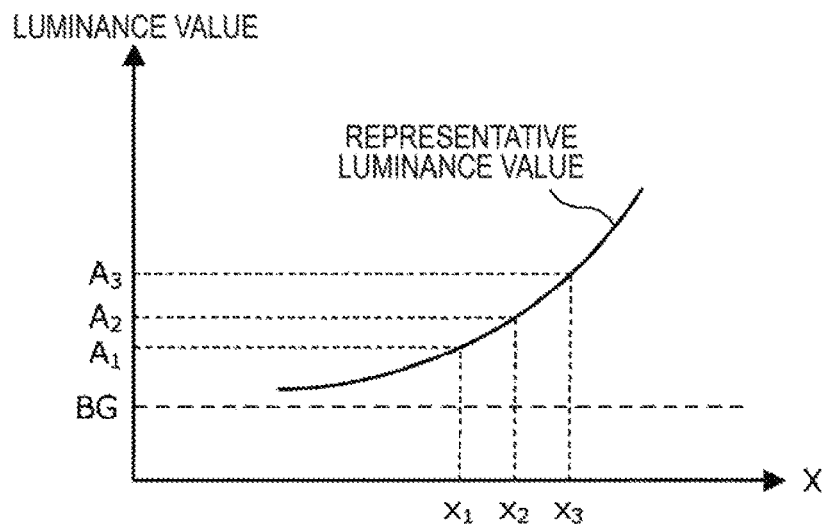
FIG. 6 is an illustrative diagram for describing an image information computation process according to the embodiment.

It is assumed that a fluorescence image is obtained by capturing fluorescence generated when the measurement subject S is excited with N (N is an integer greater than or equal to 1) photons, and as schematically illustrated in FIG. 6, a representative luminance value at a thickness position $x_i$ (i=1, 2, or 3) is denoted by $A_i$ (i=1, 2, or 3), an interval between two adjacent thickness positions is denoted by dx, and a scattering coefficient of the measurement subject S is denoted by $R_S$. If a background luminance value is set to BG for the plot of the representative luminance values illustrated in FIG. 5, the two following formulas 101 and 103 are established from a definition of the scattering coefficient $R_S$.

[Math. 1]

$$\frac{A_1 - BG}{A_2 - BG} = \exp(-N \cdot R_s \cdot dx) \quad \text{(Formula 101)}$$

$$\frac{A_2 - BG}{A_3 - BG} = \exp(-N \cdot R_s \cdot dx) \quad \text{(Formula 103)}$$

Here, if the background BG is simultaneously erased in the formulas 101 and 103, the following formula 105 can be obtained. Here, a unit of the scattering coefficient $R_S$ is [1/mm] in the following formula 105.

[Math. 2]

$$R_s = -\frac{1}{N \cdot dx} \cdot \ln\left(\frac{A_1 - A_2}{A_2 - A_3}\right) \quad \text{(Formula 105)}$$

Here, in the formula 105, N is a known parameter decided in accordance with a fluorescence microscope used when the fluorescence images are captured, dx is a known parameter set when the three representative luminance values are extracted, and $A_1$ to $A_3$ are the representative luminance values that can be obtained from the fluorescence images. Thus, the scattering coefficient $R_S$ of the measurement subject S can be computed from the representative luminance values using the formula 105.

Figure 7:
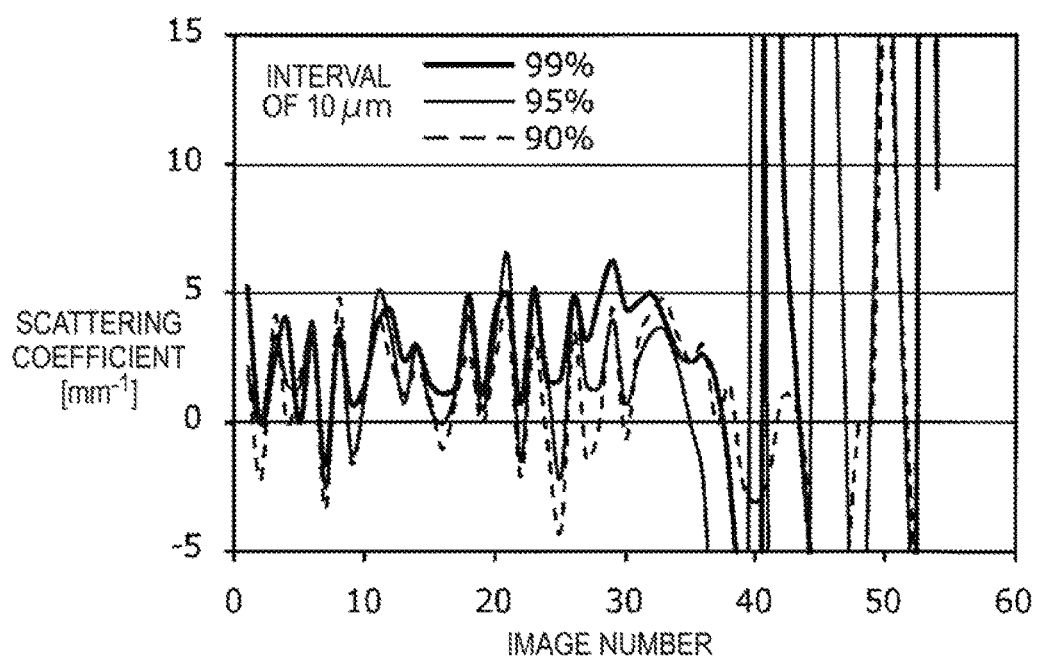
FIG. 7 is an illustrative diagram for describing an image information computation process according to the embodiment.
Figure 8:
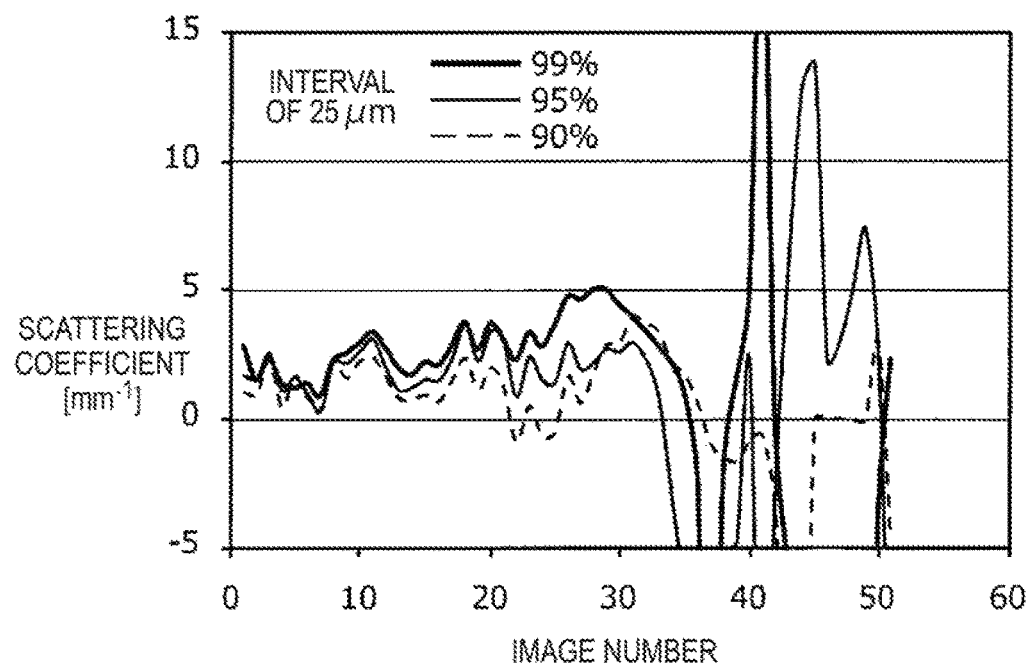
FIG. 8 is an illustrative diagram for describing an image information computation process according to the embodiment.
Figure 9:
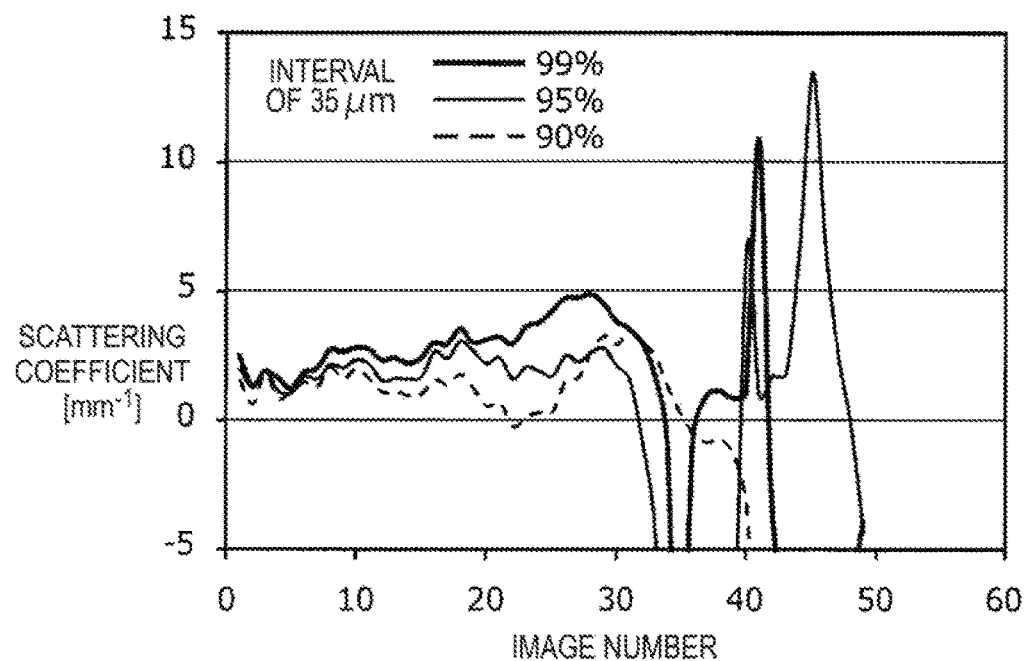
FIG. 9 is an illustrative diagram for describing an image information computation process according to the embodiment.

FIGS. 7 to 9 show scattering coefficients $R_S$ of the measurement subject S computed with the formula 105 using fluorescence images captured using a two-photon fluorescence microscope. Note that the fluorescence images are the same as those used in generating FIG. 5. Here, FIG. 7 shows computation results of the scattering coefficients $R_S$ when dx is set to 10 μm, FIG. 8 shows computation results of the scattering coefficients $R_S$ when dx is set to 25 μm, and FIG. 9 shows computation results of the scattering coefficients $R_S$ when dx is set to 35 μm.

Here, since the position corresponding to the surface is the number #43 as is obvious from FIG. 5, data from the number #43 does not include the measurement subject S and thus it is meaningless for the data to be used to measure the scattering coefficient $R_S$. In addition, with regard to the representative luminance values, a change in luminance values progresses exponentially, but it is better to note a position at which the change is expressed as exponentially as possible (i.e., at a position at which the luminance values sharply change) among positions of the representative luminance values. When the plot of "99%" of FIG. 6 is focused on, it can be ascertained that luminance values sharply change at positions of the image numbers #20 to #40. Thus, the scattering coefficient computation unit 115 sets a least uneven value at the position at which the luminance values sharply change among the scattering coefficients $R_S$ computed on the basis of the formula 105 as the scattering coefficient $R_S$ of the measurement subject S to be noted.

The result is about 5 (1/mm) at all of the positions of the numbers #20 to #40 among the results shown in FIGS. 7 to 9. Thus, the scattering coefficient computation unit 115 computes the scattering coefficient $R_S$ of the measurement subject S to be noted to be 5 (1/mm).

The scattering coefficient computation unit 115 outputs information regarding the scattering coefficient $R_S$ of the measurement subject S computed as described above to the result output unit 117 to be described below.

The result output unit 117 is realized by, for example, a CPU, a ROM, a RAM, an output device, a communication device, and the like. The result output unit 117 outputs information regarding the position of the surface of the measurement subject S specified by the surface position specifying unit 113 and information regarding the scattering coefficient $R_S$ of the measurement subject S computed by the scattering coefficient computation unit 115.

Examples of functions of the information processing device 10 according to the present embodiment have been described above. The respective constituent elements may be configured using universal members and circuits, or may be configured using hardware specialized for the functions of the constituent elements. In addition, all of the functions of the constituent elements may be fulfilled by a CPU and the like. Thus, a configuration to be used can be appropriately changed in accordance with a technical level of any occasion at which the present embodiment is implemented.

Note that a computer program for realizing each function of the information processing device according to the above-described present embodiment can be produced and installed in a personal computer and the like. In addition, a computer-readable recording medium on which the computer program is stored can also be provided. The recording medium is, for example, a magnetic disk, an optical disc, a magneto-optical disc, a flash memory, or the like. Furthermore, the computer program may be distributed through, for example, a network, without using a recording medium.

<Regarding Flow of Information Processing Method>

Figure 10:
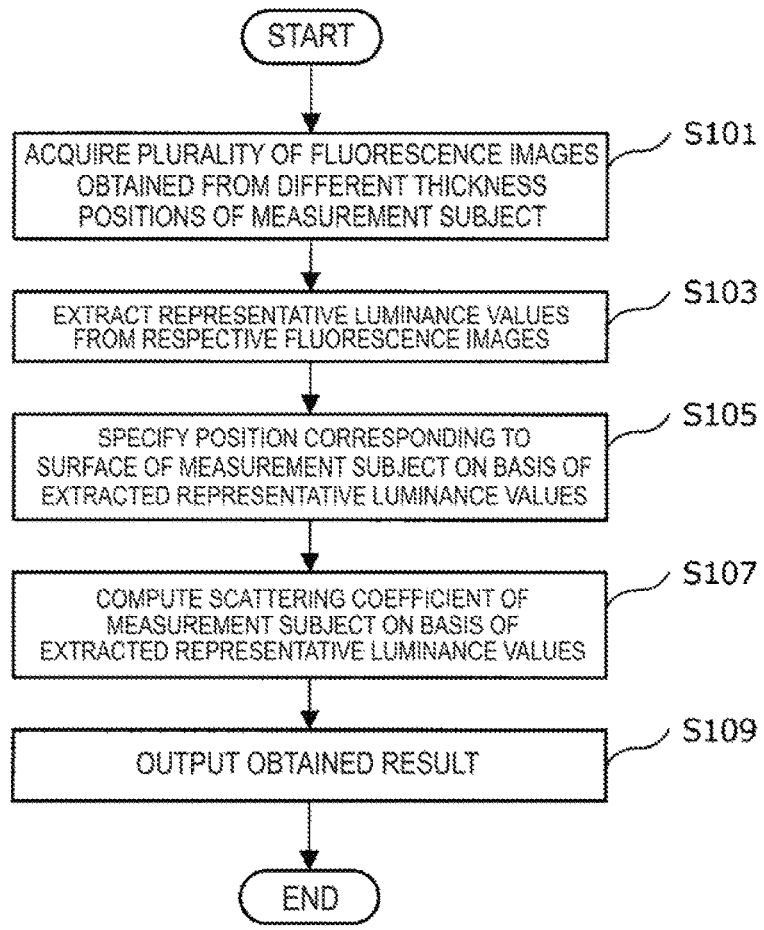
FIG. 10 is a flowchart showing an example of a flow of an information processing method according to the embodiment.

Next, an example of a flow of an information processing method executed by the information processing device 10 according to the present embodiment will be briefly described with reference to FIG. 10. FIG. 10 is a flowchart showing the example of the flow of the information processing method according to the present embodiment.

In the information processing device 10 according to the present embodiment, first, the data acquisition unit 101 acquires a plurality of fluorescence images obtained from different thickness positions of the measurement subject S (Step S101). The data acquisition unit 101 outputs information regarding the plurality of acquired fluorescence images to the representative luminance value specifying unit 111 of the image information computation unit 103.

The representative luminance value specifying unit 111 extracts representative luminance values from the plurality of respective fluorescence images using the fluorescence images output from the data acquisition unit 101 (Step S103). Then, the representative luminance value specifying unit 111 outputs information regarding the extracted representative luminance values to the surface position specifying unit 113 and the scattering coefficient computation unit 115.

The surface position specifying unit 113 specifies a position at which a maximum representative luminance value is given as a position corresponding to a surface of the measurement subject S on the basis of the extracted representative luminance values (Step S105). The surface position specifying unit 113 outputs information regarding the specified position of the surface of the measurement subject S to the scattering coefficient computation unit 115 and the result output unit 117.

In addition, the scattering coefficient computation unit 115 computes the scattering coefficient $R_S$ using the above-described formula 105 on the basis of the extracted representative luminance values (Step S107). The scattering coefficient computation unit 115 outputs information regarding the computed scattering coefficient $R_S$ to the result output unit 117.

The result output unit 117 outputs the information regarding the position of the surface specified by the surface position specifying unit 113 and the information regarding the scattering coefficient computed by the scattering coefficient computation unit 115 to the outside (Step S109). Accordingly, a user of the information processing device 10 can ascertain image information regarding the fluorescence images of the measurement subject S.

The example of the flow of the information processing method according to the present embodiment has been briefly described above with reference to FIG. 10.

According to the information processing device 10 and the information processing method of the present embodiment as described above, a surface position specifying method that does not depend on visual observation (in other words, that does not depend on a technique of a user) can be provided.

In addition, by directly analyzing a fluorescence image using the information processing device 10 and the information processing method according to the present embodiment, the scattering coefficient $R_S$ of the measurement subject S can be computed. If the scattering coefficient $R_S$ of the measurement subject S is known, an intensity (power) necessary for acquiring a fluorescence image can be estimated, and thus important information for appropriately acquiring a fluorescence image can be obtained.

Furthermore, since a scattering coefficient has a possibility of having a relation with a state of a cell such as fibrosis, there is a possibility of a measurement of a scattering coefficient serving as an index for evaluating a function of an organ. Using the information processing device 10 and the information processing method according to the present embodiment, the scattering coefficient $R_S$ can be computed if information can be acquired through observation from one side of the measurement subject S and the measurement subject S has a thickness of about dozens micrometers. Thus, using the information processing device 10 and the information processing method according to the present embodiment, even information of an organ having high tissue porosity such as a lung can be acquired, and information can be acquired from a small tissue sample from an organ such as a liver.

With regard to a degree of a margin with which a cancer tissue is to be excised in a surgery for a digestive organ cancer such as a liver cancer, a doctor ascertains a degree of inflammation or induration of the organ during the surgery and excises a sufficient area of the cancer tissue securing an extra margin if there is likely to be little induration, or leaves a large area of an organ tissue having a small margin if there is likely to be induration. When the surgery is a laparotomy, the doctor ascertains a degree of inflammation or induration of an organ of a patient by touching the organ with his or her hand or visually checking the organ. However, as endoscopic surgeries have developed in recent years, minimally invasive endoscopic surgeries have been used most frequently. Here, there also is a method of transcutaneously diagnosing hardness of a liver using ultrasonic waves (elastography), however, elastography is very expensive and thus using the technique in an operating room of a gastroenterological surgery is not normal. Thus, a degree of inflammation or induration of a liver of a patient is normally ascertained only using a technique of determining the degree of inflammation or induration by color using a camera in endoscopic surgery. For this reason, accuracy of information on a liver function of a patient is lower than a recovery surgery performed in the past, and thus a risk of excising a large margin even though induration has progressed or the like is heightened.

Here, it has been reported that cancerous organs have scattering coefficients or absorption coefficients that are about 15% lower than those of normal tissues, and since the information processing device 10 and the information processing method according to the present embodiment can compute a scattering coefficient of a tissue from a fluorescence image, there is great merit in deciding a position to be excised and an intraoperative diagnosis of a cell in a gastroenterological surgery. In addition, the merit also contributes to the discovery of cancer cells in respiratory internal medicine, respiratory surgery, and urology. As described above, the information processing device 10 and the information processing method according to the present embodiment also provide useful information in the field of medicine.

Second Embodiment

Next, as a second embodiment of the present disclosure, an image acquisition system that has an imaging function of imaging a fluorescence image of a measurement subject and the function of computing image information including a position of a surface and a scattering intensity of a measurement subject described in the first embodiment will be described in detail with reference to FIGS. 11 to 23.

As will be described in detail, in the image acquisition system according to the present embodiment, fluorescence images are acquired using an image guide fiber constituted by a plurality of optical fiber element wires. The present inventor has separately reviewed a method for detecting fluorescence generated through a multi-photon excitation process in order to use such an image guide fiber. As a result, the present inventor has gained knowledge that, in order to increase luminance of fluorescence through the multi-photon excitation process, it is preferable that a guided wave of excitation light using an image guide fiber is in a single mode (more specifically, a zero-order mode) and, if an image guide fiber constituted by optical fiber element wires in a multi-mode is used as it is, a decrease or unevenness in luminance of the fluorescence occurs so as to make it impossible to acquire a fluorescence image using a multi-photon excitation process.

Here, when fluorescence in a multi-photon excitation process is measured using an image guide fiber, optical fiber element wires constituting the image guide fiber are also considered to be set as optical fiber element wires in a single mode. In this case, in order to reduce crosstalk between adjacent optical fiber element wires when the optical fiber element wires in the single mode are used, it is necessary to reduce a difference in refractive index between a core and a cladding of the optical fiber. However, reducing the difference in refractive index between the core and the cladding means an increase in diffusion of electric field intensity distribution toward the cladding. Thus, in order to reduce crosstalk between adjacent optical fiber element wires, it is important to widen intervals between the adjacent optical fiber element wires.

Resolution of the image guide fiber depends on arrangement intervals of the optical fiber element wires, and as the arrangement intervals of the optical fiber element wires are narrowed, the resolution obtained is increased. Thus, when the optical fiber element wires in the single mode are used and intervals of the optical fiber element wires are widened, while another mechanism that scans the optical fiber to obtain the same degree of resolution as that of a normal image guide fiber is necessary, it is difficult to narrow a diameter of the optical fiber element wires.

Furthermore, reducing the difference in refractive index between the core and the cladding of the optical fiber leads a numerical aperture (NA) of the optical fiber element wires being lowered, and thus in order to acquire a signal of fluorescence in a multi-photon excitation process with high efficiency, an effort of using a double-clad fiber or the like is important.

On the basis of the above-described knowledge, the present inventor has intensively investigated an image acquisition system which can acquire a fluorescence image using stable multi-photon excitement even when an image guide fiber composed of optical fiber element wires in a multi-mode is used. As a result, the present inventor found that (1) if a single mode is excited on an incident end face of an image guide fiber, there is a case in which fluorescence probably reaches a sample-side end face in the single mode, and (2) data of excitation light that has reached the sample-side end face in the single mode can be acquired by acquiring images a plurality of times and selecting the highest fluorescence value, and thus the present inventor has developed an image acquisition system according to the second embodiment of the present disclosure to be described below.

<Regarding Image Acquisition System>
[Overall Configuration of Image Acquisition System]

Figure 11:
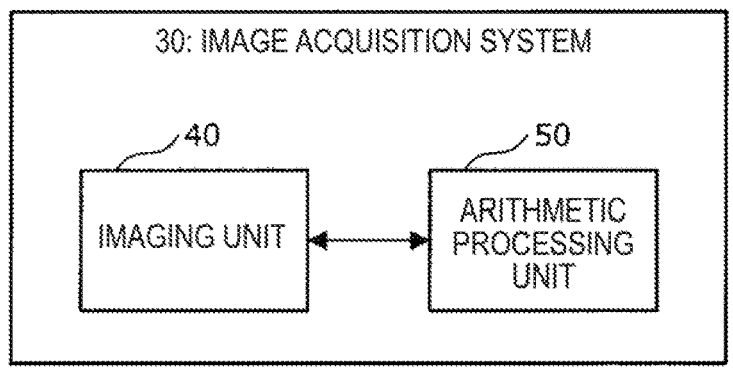
FIG. 11 is a block diagram showing an example of a configuration of an image acquisition system according to a second embodiment of the present disclosure.

First, an overall configuration of an image acquisition system 30 according to the second embodiment of the present disclosure completed on the basis of the above-described knowledge will be described with reference to FIG. 11. FIG. 11 is an illustrative diagram schematically showing a configuration of the image acquisition system according to the present embodiment.

The image acquisition system 30 according to the present embodiment is a system which radiates excitation light having a predetermined wavelength toward a measurement subject that is an observation target to generate fluorescence from the measurement subject in a multi-photon excitation process, acquires a captured image of the imaging subject based on the fluorescence, and computes image information as described in the first embodiment on the basis of the obtained captured image. The image acquisition system 30 has an imaging unit 40 and an arithmetic processing unit 50 as illustrated in FIG. 11.

The imaging unit 40 is a unit which radiates the excitation light having a predetermined wavelength toward the measurement subject, detects fluorescence generated through a multi-photon excitation process, and thereby generates image data regarding the generated fluorescence. The image data generated by the imaging unit 40 is output to the arithmetic processing unit 50. Details of a configuration of the imaging unit 40 will be described below.

The arithmetic processing unit 50 is a unit which comprehensively controls imaging processing on the measurement subject that is performed by the imaging unit 40, performs an arithmetic process to be described below on the image data generated by the imaging unit 40, generates a captured image of the measurement subject, and computes image information thereof.

The arithmetic processing unit 50 may be an information processing device such as any of a variety of computers or servers provided outside the imaging unit 40, or may be an arithmetic chip that is installed in the imaging unit 40 and composed of a CPU, a ROM, a RAM, and the like.

Details of a configuration of the arithmetic processing unit 50 will be described below.

[Configuration of Imaging Unit 40]

Next, details of a configuration of the imaging unit 40 according to the present embodiment will be described with reference to FIGS. 12 to 18B.

Figure 12:
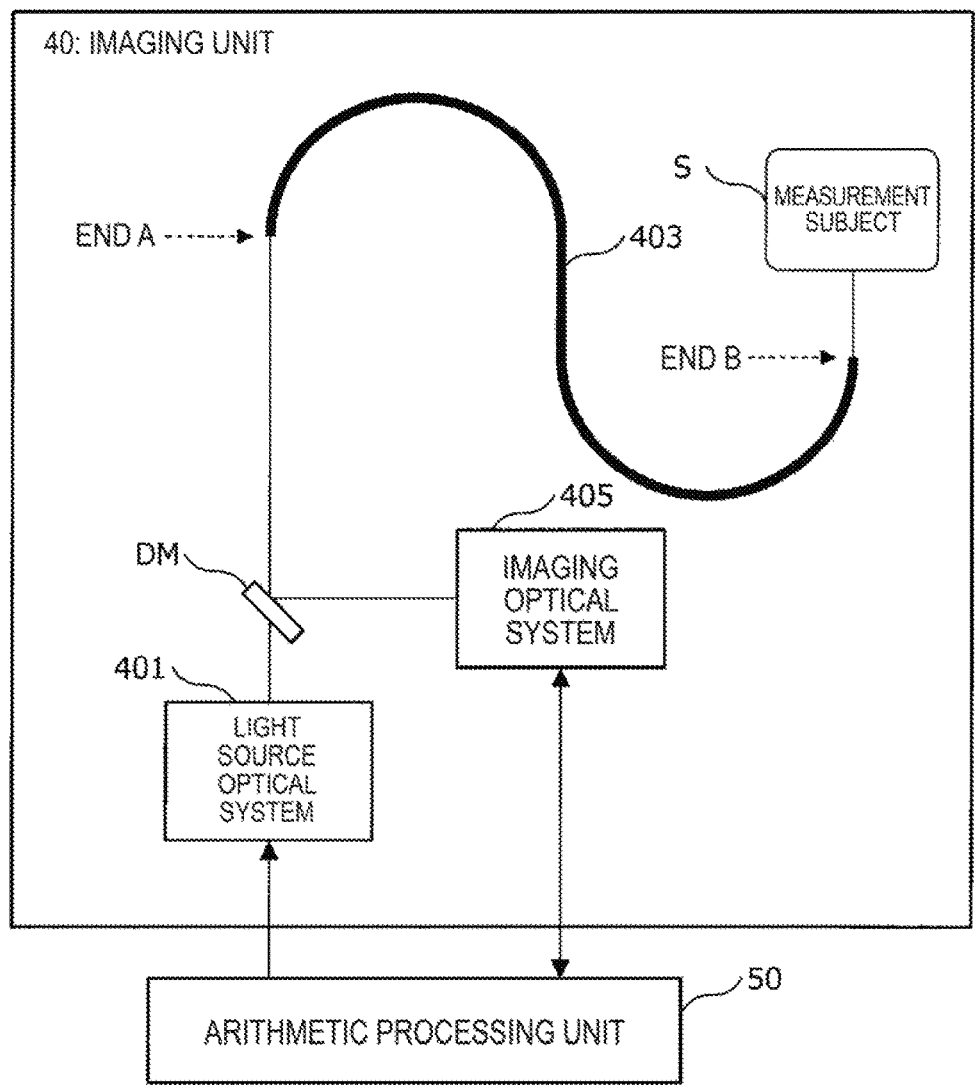
FIG. 12 is an illustrative diagram schematically showing an example of a configuration of an imaging unit according to the embodiment.
Figure 17:
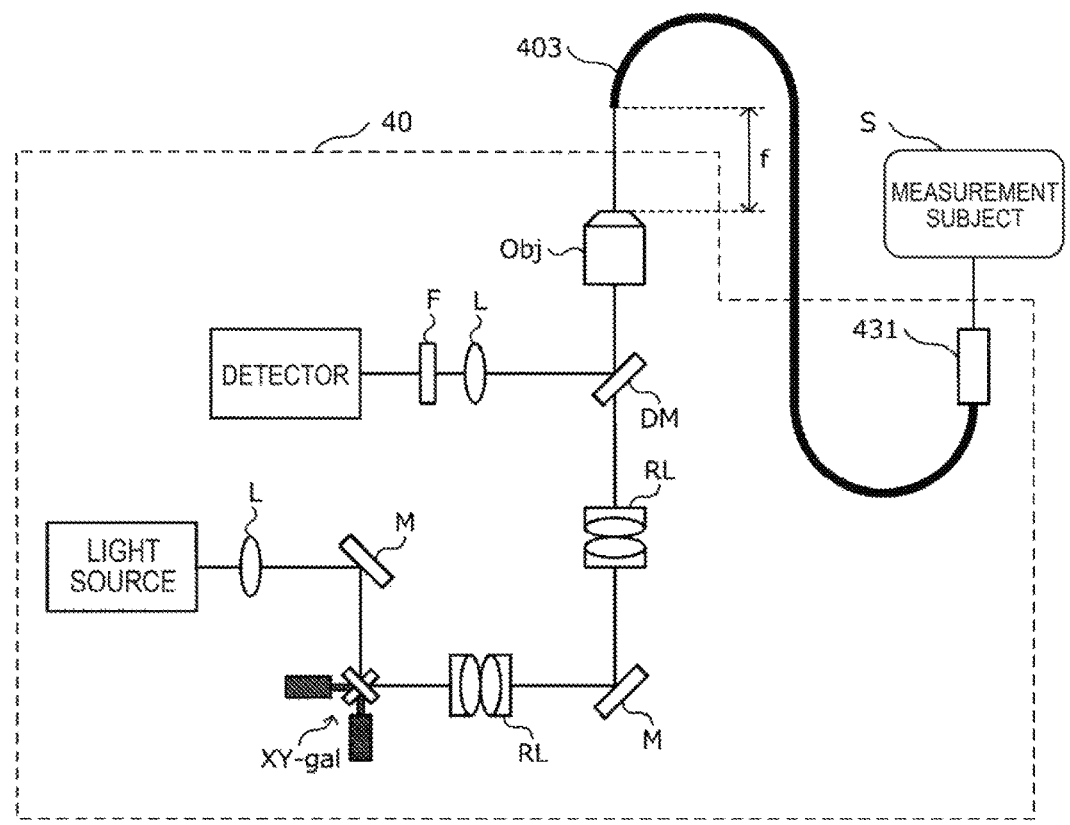
FIG. 17 is an illustrative diagram schematically showing a specific example of the imaging unit according to the embodiment.
Figure 18A:
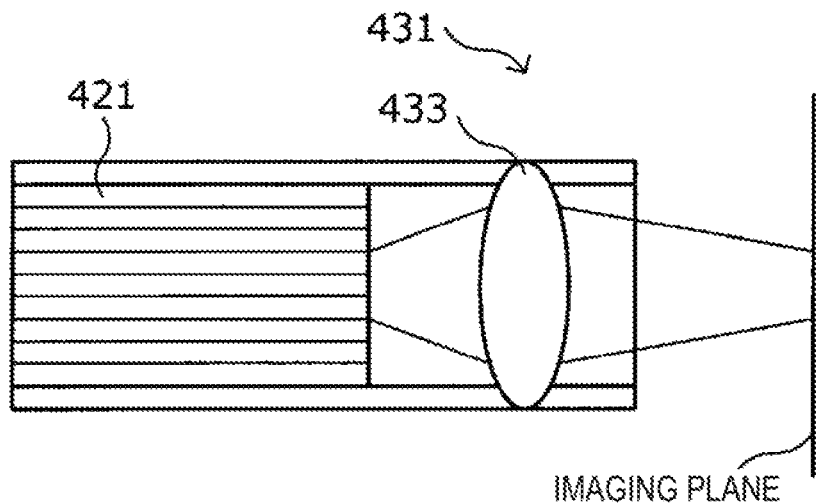
FIG. 18A is an illustrative diagram for describing an end unit of the image guide fiber according to the embodiment.
Figure 18B:
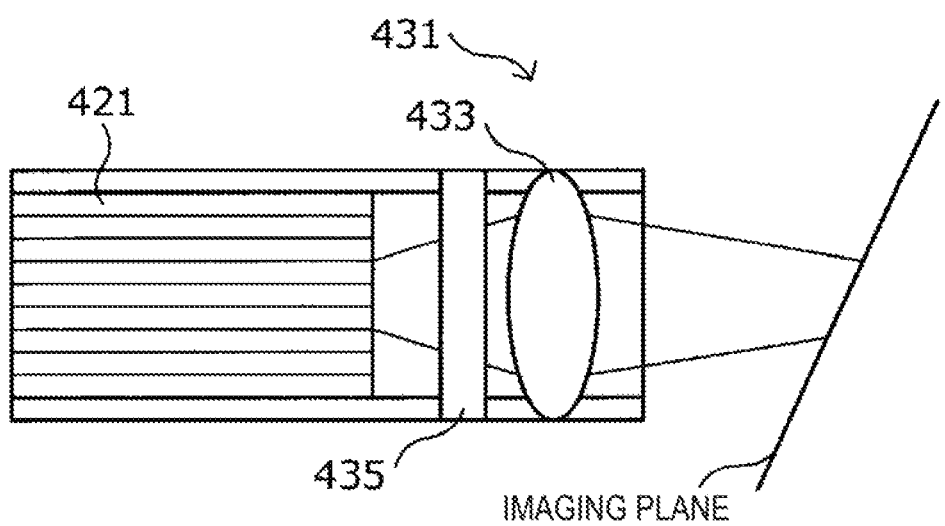
FIG. 18B is an illustrative diagram for describing an end unit of the image guide fiber according to the embodiment.

FIG. 12 is an illustrative diagram schematically showing an example of the configuration of the imaging unit according to the present embodiment. FIGS. 13A to 13D are illustrative diagrams schematically showing examples of a light source provided in the imaging unit according to the present embodiment. FIG. 14 is an illustrative diagram schematically showing a structure of an image guide fiber provided in the imaging unit according to the present embodiment. FIGS. 15A to 15D are illustrative diagrams for describing mode excitation when light converges on an end face of a multi-mode optical waveguide. FIGS. 16A and 16B are illustrative diagrams schematically showing scanning methods of the image guide fiber of the imaging unit according to the present embodiment. FIG. 17 is an illustrative diagram schematically showing a specific example of the imaging unit according to the present embodiment. FIGS. 18A and 18B are illustrative diagrams for describing an end unit of the image guide fiber according to the present embodiment.

The imaging unit 40 of the image acquisition system 30 according to the present embodiment mainly has a light source optical system 401, an image guide fiber 403, and an imaging optical system 405 as illustrated in FIG. 12.

The light source optical system 401 is an optical system which guides excitation light having a predetermined wavelength for generating fluorescence by exciting the measurement subject S with two or more photons (i.e., excitation using multiple photons) toward the measurement subject S. The light source optical system 401 is constituted by a laser light source which emits the excitation light having a predetermined wavelength and optical elements such as various lenses, various mirrors, and various filters that guide the excitation light emitted from the light source toward the measurement subject S.

A detailed disposition of the various optical elements in the light source optical system 401 is not particularly limited, and a disposition of a known optical system can be employed.

In addition, a laser light source of the light source optical system 401 is also not particularly limited, and any of a variety of light sources such as various semiconductor lasers, solid-state lasers, and gas lasers can be used. By using a light source which uses any of a variety of semiconductor light sources as the laser light source, the image acquisition system 30 can be further miniaturized.

A semiconductor laser and a light source which uses a wavelength conversion unit which converts a wavelength of light of the semiconductor laser as illustrated in FIG. 13A to 13D can be used, for example, as a light source which uses a semiconductor laser that can be used as the laser light source unit of the light source optical system 401.

Figure 13A:
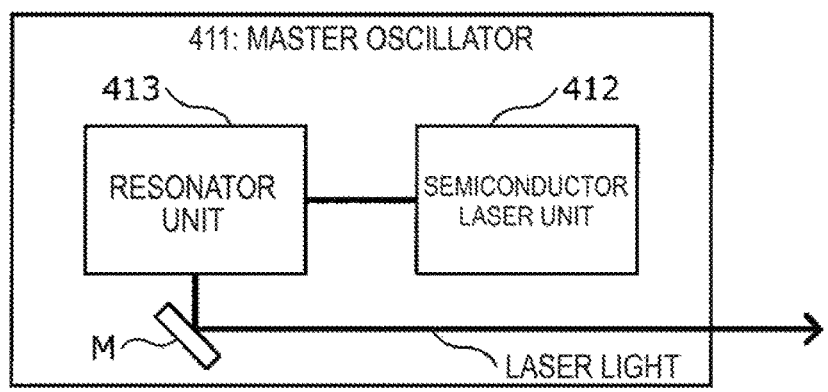
FIG. 13A is an illustrative diagram schematically showing an example of a light source provided in the imaging unit according to the embodiment.
Figure 14:
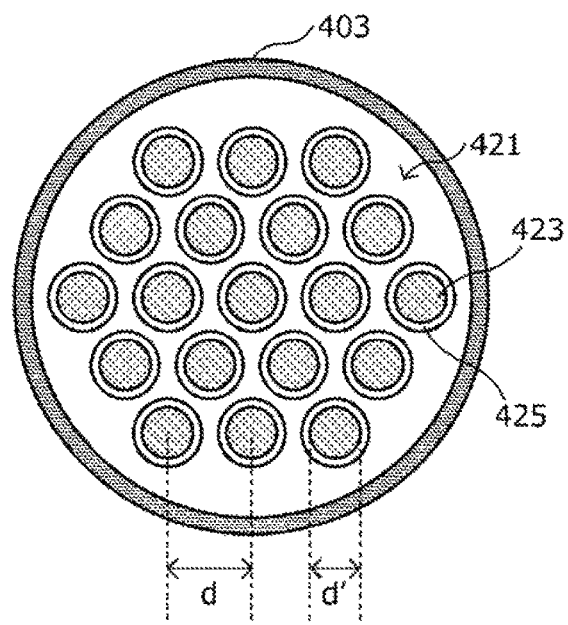
FIG. 14 is an illustrative diagram schematically showing a structure of an image guide fiber provided in the imaging unit according to the embodiment.

FIG. 13A schematically illustrates a master oscillator 411, which is constituted by a semiconductor laser and a resonator, as an example of a semiconductor laser that can be used in the laser light source unit. The master oscillator 411 provided as the laser light source unit is constituted by a semiconductor laser unit 412 that can emit laser light having a predetermined wavelength (e.g., a wavelength of 405 nm)

and a resonator unit 413 for amplifying the laser light emitted from the semiconductor laser unit 412.

Figure 13B:
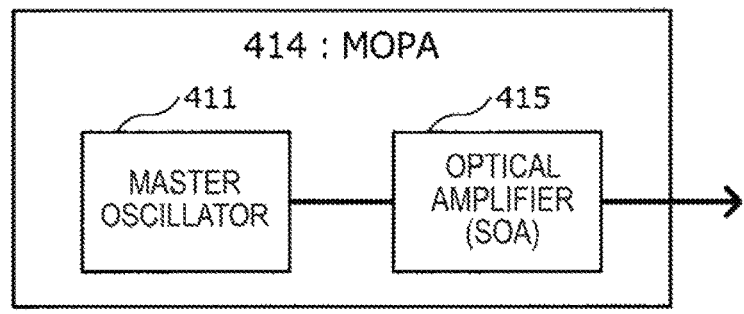
FIG. 13B is an illustrative diagram schematically showing an example of a light source provided in the imaging unit according to the embodiment.

FIG. 13B schematically illustrates a master oscillator power amplifier (MOPA) 414, which is constituted by a master oscillator and an optical amplifier, as an example of a semiconductor laser that can be used in the laser light source unit. In the light source, an optical amplifier 415 for further amplifying the emitted laser light is provided in a later stage of the master oscillator 411 illustrated in FIG. 13A. A semiconductor optical amplifier (SOA) or the like can be preferably used, for example, as the optical amplifier 415.

Figure 13C:
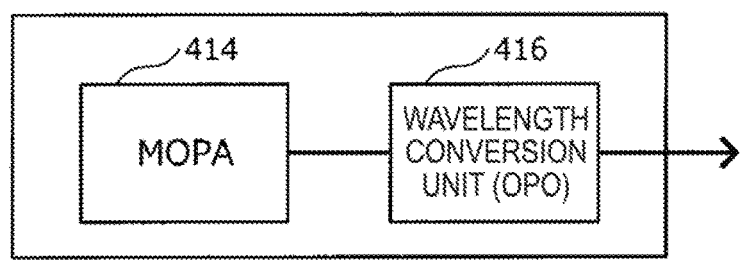
FIG. 13C is an illustrative diagram schematically showing an example of a light source provided in the imaging unit according to the embodiment.
Figure 13D:
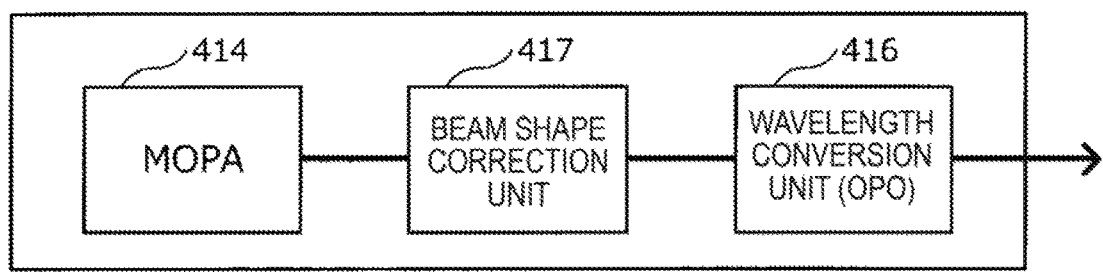
FIG. 13D is an illustrative diagram schematically showing an example of a light source provided in the imaging unit according to the embodiment.

FIG. 13C schematically illustrates a light source, which has the MOPA 414 and a wavelength conversion unit, as an example of a semiconductor laser that can be used in the laser light source unit. In the light source, a wavelength conversion unit 416 for converting a wavelength of laser light which has had its intensity amplified is provided in a later stage of the optical amplifier 415 illustrated in FIG. 13B. An optical parametric oscillator (OPO) which uses various types of non-linear crystals or the like can be preferably used, for example, as the wavelength conversion unit 416. In addition, by providing a beam shape correction unit 417 which corrects beam shapes of laser light between the MOPA 414 and the wavelength conversion unit 416 as illustrated in FIG. 13D, wavelength conversion efficiency of the wavelength conversion unit 416 can be further improved.

In addition, a wavelength of excitation light emitted from the laser light source is not particularly limited, and a wavelength suitable for exciting a fluorescent substance included in the measurement subject S may be appropriately selected. Further, a laser to be used as the light source may be a continuous wave (CW) laser or a pulse laser.

The image guide fiber 403 is formed by bundling a plurality of multimode optical fiber element wires 421 as schematically illustrated in FIG. 14. Each of the optical fiber element wires 421 is formed of a core 423 that can guide light of a zero-order mode but also light of a higher-order mode, and a cladding 425 provided to cover the core 423. The optical fiber element wires 421 are disposed to have a hexagonal close-packed structure as schematically illustrated in FIG. 14 so far as possible. A separation distance d between adjacent optical fiber element wires 421 may be appropriately set in accordance with image resolution to be obtained, and, for example, a value such as 3.5 μm may be possible. In addition, a diameter d' of the core 423 may also be appropriately set, and, for example, a value such as 3 μm may be possible.

The image guide fiber 403 transmits excitation light from the light source optical system 401 incident on one end (e.g., an end A in FIG. 12) to the measurement subject S, and transmits an image of the measurement subject S formed on the other end (e.g., an end B in FIG. 12) using fluorescence generated from the measurement subject S to the one end (e.g., the end A in FIG. 12).

The imaging optical system 405 scans the image of the measurement subject S transmitted to the end (e.g., the end A in FIG. 12) of the image guide fiber 403 at a scanning pitch that is narrower than a size of the core 423 (the core diameter d' in FIG. 14) of each of the plurality of optical fiber element wires 421. At this time, the imaging optical system 405 performs imaging such that at least a part of an optical fiber element wire-corresponding image which corresponds to each of the optical fiber element wires 421 is included in a plurality of images, and generates a plurality of pieces of image data of the measurement subject S.

The imaging optical system 405 is constituted by various detectors which detect an image (i.e., a fluorescence signal corresponding to generated fluorescence) of the measurement subject S transmitted from the image guide fiber 403, and optical elements such as various lenses, various mirrors, various filters, and the like which guide the image (fluorescence signal) of the measurement subject S toward the detectors.

A detailed disposition of the various optical elements of the imaging optical system 405 is not particularly limited, and a disposition of a known optical system can be employed.

Known detectors can also be used as the detectors provided in the imaging optical system 405 as long as they can convert information regarding intensity of fluorescence into an electric signal. Various detectors such as a charge-coupled device (CCD), a photomultiplier tube (PMT), and the like can be exemplified, for example, as the detector.

In addition, a mechanism for scanning the end faces of the image guide fiber 403 as will be described in detail below is provided in at least any one of the light source optical system 401 and the imaging optical system 405 shown in FIG. 12. Such a scanning mechanism is not particularly limited, and, for example, a known mechanism such as a galvano mirror can be used.

The configuration of the imaging unit 40 according to the present embodiment has been described above in detail with reference to FIGS. 12 to 14.

[Scanning Method of Image Guide Fiber]

Next, a scanning method of an end face of the image guide fiber 403 by the imaging optical system 405 will be described with reference to FIGS. 15A to 16B.

First, mode excitation when light converged on an end face of a multimode optical waveguide used in an image guide will be described with reference to FIGS. 15A to 15D.

Figure 15A:
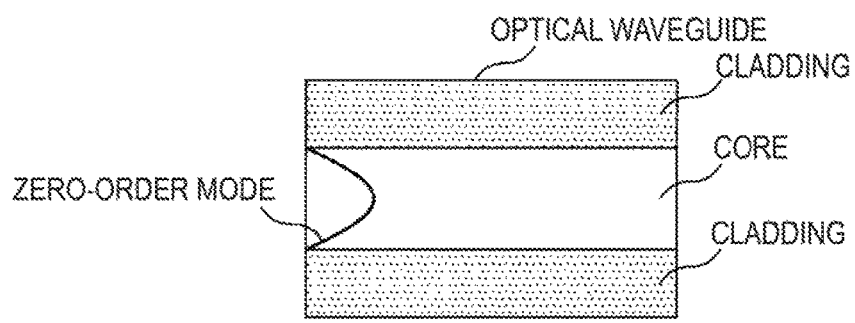
FIG. 15A is an illustrative diagram for describing mode excitation when light converges on an end face of a multi-mode optical waveguide.
Figure 15B:
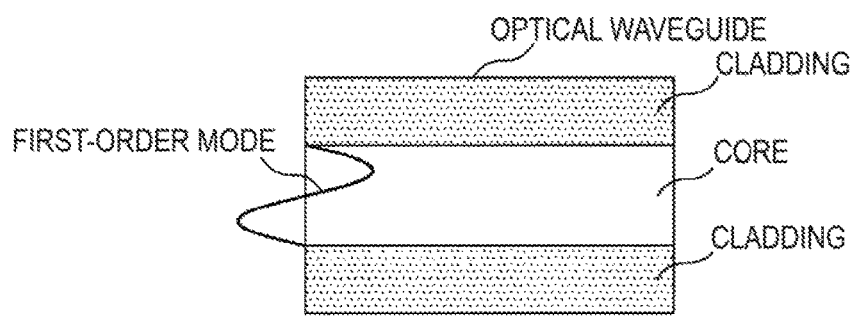
FIG. 15B is an illustrative diagram for describing mode excitation when light converges on an end face of a multi-mode optical waveguide.

In the multimode optical waveguide (s multimode optical fiber), even when an optical fiber that guides waves in a zero-order mode as illustrated in FIG. 15A and a first-order mode (a higher-order mode) as illustrated in FIG. 15B is used, the modes have orthogonality. Thus, as long as perturbation caused from the outside, for example, like when there is a flaw on the optical waveguide, is not exerted, propagation occurs on the optical waveguide (optical fiber) in the zero-order mode without change in the case of the zero-order mode, and propagation also occurs on the optical waveguide in the first-order mode without change in the case of the first-order mode.

Next, states of coupling of waveguide modes inside a fiber when light from the outside is coupled on an end face of the fiber (when light which passes through a lens converges on the end face of the optical fiber) will be described with reference to FIGS. 15C and 15D. A convolution integral of an electric field strength distribution of convergence spots and an electric field strength distribution of waveguide modes are used to decide which waveguide mode will be excited in the inside of the fiber.

Figure 15C:
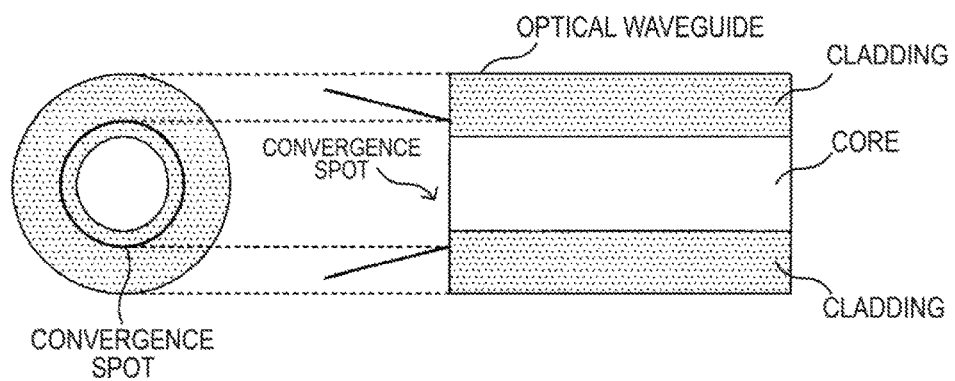
FIG. 15C is an illustrative diagram for describing mode excitation when light converges on an end face of a multi-mode optical waveguide.
Figure 15D:
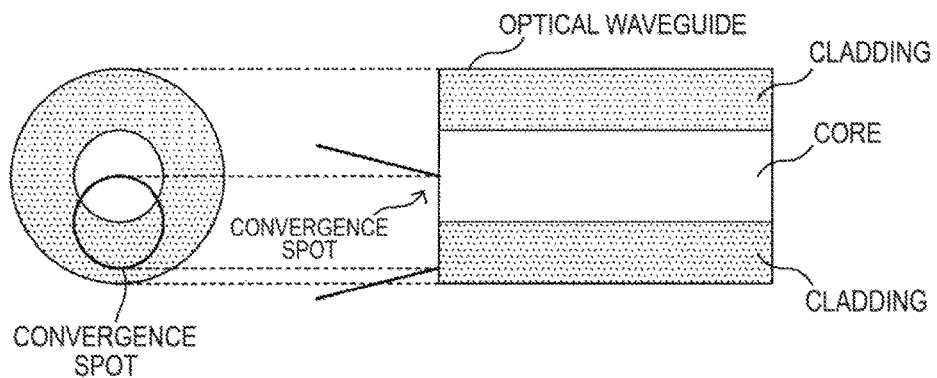
FIG. 15D is an illustrative diagram for describing mode excitation when light converges on an end face of a multi-mode optical waveguide.

As illustrated in FIG. 15C, when a convergence spot coincides with the center of the core and a size of the spot approximates a size of the core, an electric field distribution of the convergence spot substantially matches an electric field distribution of the zero-order mode illustrated in FIG. 15A, and thus the zero-order mode is excited in the inside of the fiber. In addition, since the electric field strength distribution illustrated in FIG. 15B has a different sign at the center, the electric field strength distribution illustrated in FIG. 15C and the electric field strength distribution of the first-order mode illustrated in FIG. 15B have an integrated value that is substantially zero, and thus the first-order mode is not excited. On the other hand, when the convergence spot is shifted from the center of the core as illustrated in FIG. 15D, a convolution integral of the electric field strength distribution illustrated in FIG. 15D and the first-order mode illustrated in FIG. 15B are not zero, thus the first-order mode is excited at a certain ratio, and a ratio at which the zero-order mode is excited decreases accordingly. Thus, the zero-order mode is excited on the incident end face when the zero-order mode is dominantly excited on the incident end face as illustrated in FIG. 15C, and since the waveguide mode of the optical waveguide has orthogonality, light is guided toward the emission end inside the optical fiber without change in the zero-order mode.

The present inventor has ascertained that, if a single mode (the zero-order mode) is excited on an incident end face of an image guide fiber, a case in which light probably reaches the sample-side end face in a single mode exists, and thus the present inventor has conceived a scanning method for an end face of the image guide fiber 403 as schematically illustrated in FIGS. 16A and 16B.

In other words, the imaging unit 40, according to the present embodiment scans an end face of the image guide fiber 403 (e.g., the end face of the end A in FIG. 12) at a scanning pitch that is narrower than a size of a core of each of a plurality of optical fiber element wires.

For example, FIG. 16A illustrates an example in which scanning is performed at a pitch p that is narrower than the size d' of a core of each optical fiber element wire 421 in a direction parallel to a scanning direction of an end face of the image guide fiber 403. In this case, a position of an axis expressing the scanning direction (a scanning axis) is set in advance in accordance with a diameter of the image guide fiber 403 to be used and the core diameter d' of each optical fiber element wire 421, and the end face of the image guide fiber 403 is captured at positions of black circles in FIG. 16A under control of the arithmetic processing unit 50. At this time, although imaging intervals in the direction parallel to the scanning direction are controlled by the arithmetic processing unit 50 on the basis of the scanning pitch p, imaging intervals in a direction orthogonal to the scanning direction are controlled on the basis of an interval d of the adjacent optical fiber element wires 421 of the image guide fiber 403. In the scanning method shown in FIG. 16A, the entire measurement subject S is captured one time under the above-described control. In other words, in the scanning method shown in FIG. 16A, a frequency of image data generated through imaging (a data restoration frequency) is higher than the number of optical fiber element wires 421.

In addition, for example, FIG. 16B illustrates an example in which scanning is performed at the pitch p that is narrower than the size d' of the core of each of the optical fiber element wires 421 in the direction orthogonal to the scanning direction of an end face of the image guide fiber 403. In this case, a position of an axis expressing the scanning direction (a scanning axis) is set in advance in accordance with the diameter of the image guide fiber 403 to be used and the core diameter d' of each of the optical fiber element wires 421, and the end face of the image guide fiber 403 is captured at positions of black circles in FIG. 16B under control of the arithmetic processing unit 50. At this time, although the imaging intervals in the direction parallel to the scanning direction are controlled by the arithmetic processing unit 50 on the basis of the interval d of the adjacent optical fiber element wires 421 of the image guide fiber 403, the imaging intervals in the direction orthogonal to the scanning direction are controlled on the basis of the scanning pitch p. In the scanning method shown in FIG. 16B, the entire measurement subject S is captured a plurality of times (e.g., 5 times in the example of FIG. 16B) under the above-described control. In other words, in the scanning method shown in FIG. 16B, a frequency of data restoration in one scanning corresponds to the number of optical fiber element wires 421, and reference positions (scanning start positions) in each scanning process change at the pitch p that is narrower than a disposition pitch of the optical fiber element wires 421.

Note that "imaging" in the above description means forming an image at the position of the black circles in FIGS. 16A and 16B with excitation light guided by the light source optical system 401, and capturing an image (a fluorescence image) transmitted to an end face of the image guide fiber 403 at the positions of the black circles.

As the above-described scanning method is realized, at least a part of areas corresponding to the optical fiber element wires 421 (which will also be referred to as an "optical fiber element wires-corresponding area" below) is captured and included in a plurality of images.

By scanning the end face of the image guide fiber 403 as illustrated in FIGS. 16A and 16B, a plurality of pieces of image data generated through imaging processes include image data of a case in which excitation light is radiated to all cores. In this situation, a fundamental wave (the zero-order mode) is excited at the core of the image guide fiber 403, and thus there also is a case in which the fundamental wave probably reaches a sample-side end face.

Note that the imaging unit 40 may perform an imaging process only one time at each of the imaging positions illustrated in FIGS. 16A and 16B, and may perform the imaging process a plurality of times at each of the imaging positions to increase a probability.

In addition, it is a matter of course that the imaging unit 40 according to the present embodiment may employ a scanning method obtained by combining the methods of FIG. 16A and FIG. 16B (i.e., the scanning methods at the scanning pitch p in the scanning direction and the direction orthogonal to the scanning direction).

A specific size of the scanning pitch p shown in FIGS. 16A and 16B may be appropriately set in accordance with the core diameter d' of the optical fiber element wire 421, and a size of about 1/10 of the core diameter d' or smaller is preferable. As a result of a review of the present inventor, by setting the scanning pitch p to be 1/10 of the core diameter d' or smaller, (e.g., when the core diameter d' is 3 μm, the scanning pitch p is set to be 0.3 μm or smaller), it is possible to obtain luminance of 86% or more of the maximum luminance obtained through excitation by the optical fiber element wires 421. In addition, by setting the scanning pitch p to be 1/12 of the core diameter of d' or smaller, it is possible to obtain luminance of 90% or more of the maximum luminance obtained through excitation by the optical fiber element wires 421.

Note that the scanning directions and imaging positions shown in FIGS. 16A and 16B and the number of scanning operations shown in FIG. 16B are merely examples, and the present invention is not limited to the examples shown in FIGS. 16A and 16B.

The examples of the scanning methods for an end face of the image guide fiber 403 according to the present embodiment have been described above in detail with reference to FIGS. 16A and 16B.

[Specific Example of Imaging Unit 40]

A specific example of the imaging unit 40 according to the present embodiment will be briefly described with reference to FIGS. 17 to 18B.

As illustrated in FIG. 17, for example, excitation light computed from one of the light sources illustrated in FIGS. 13A to 13D is guided toward an XY galvano mirror XY-gal via a lens L and a mirror M, and the galvano mirror controls an image formation position with respect to the image guide fiber 403. Excitation light that has gone through the galvano mirror goes through a relay lens RL, the mirror M, and a dichroic mirror DM, and is guided to an object lens Obj. Here, one end of the above-described image guide fiber 403 is arranged at a focal position f of the object lens Obj.

It is preferable to provide an end unit 431 to be described below at the other end of the image guide fiber 403. Accordingly, fluorescence images of the measurement subject S having different positions in a thickness direction can be easily obtained. Fluorescence is generated from the measurement subject S by the excitation light that has passed through the image guide fiber 403 and the end unit 431 and has been guided to the measurement subject S. The generated fluorescence passes through the end unit 431, the image guide fiber 403, the object lens Obj, the dichroic mirror DM, another lens L, a notch filter F, and the like, and is guided to a photomultiplier serving as a detector or the like.

Here, with respect to the imaging unit 40 according to the present embodiment, it is important to acquire fluorescence images while changing a position of the measurement subject S in the thickness direction (i.e., changing a focal position thereof). Here, as a method for changing a focal position, moving a lens 433 installed at a leading end of the optical fiber element wires 421 in the end unit 431 or moving the whole end unit 431 to move a coupling face of the lens 433 as illustrated in FIG. 18A is considered. Accordingly, it is possible to acquire fluorescence images which have different observation positions in the depth direction.

In the method of moving the lens 433, however, it is necessary to provide a driving mechanism (not illustrated) in the end unit 431, but it is not easy to make a driving mechanism having a narrower diameter, there are cases in which narrowing a diameter of the end unit 431 is challenging. In addition, in the method of moving the whole end unit 431, it is not easy to move the end unit 431 at predetermined intervals, and thus there is a possibility of an error being made in computation of a scattering coefficient as described in the first embodiment.

Thus, in the imaging unit 40 according to the present embodiment, it is preferable to provide an optical component 435 for a hologram that can simultaneously acquire fluorescence from different thickness positions of the measurement subject S between the optical fiber element wires 421 and the lens 433 as illustrated in FIG. 18B. A spatial light modulator (SLM) disclosed in Non-Patent Literatures 2 and 3, a quadratically distorted grating disclosed in Non-Patent Literature 4, or the like can be exemplified, for example, as the optical component 435. By providing the optical component 435, fluorescence from different thickness positions can be acquired in a short period of time such that an imaging plane having different depths is realized without providing a driving mechanism.

Note that, when the optical component 435 illustrated in FIG. 18B is used, an amount of information regarding the fluorescence at the thickness positions is smaller than the case in which the end unit 431 is used as illustrated in FIG. 18A. Thus, when the end unit 431 is used as illustrated in FIG. 18B, it is preferable to increase an amount of information regarding the fluorescence at the thickness positions by using the image guide fiber 403 that has as many pixels as possible or by rotating the image guide fiber 403 and then reacquiring the images. Note that, when the image guide fiber 403 is rotated, a direction in which the thickness positions are different is also rotated in accordance with the rotation of the image guide fiber 403 without needing to provide a driving mechanism in the end unit 431.

[Overall Configuration of Arithmetic Processing Unit 50]

Next, a configuration of the arithmetic processing unit 50 included in the image acquisition system 30 according to the present embodiment will be described in detail with reference to FIGS. 19 to 23.

Figure 19:
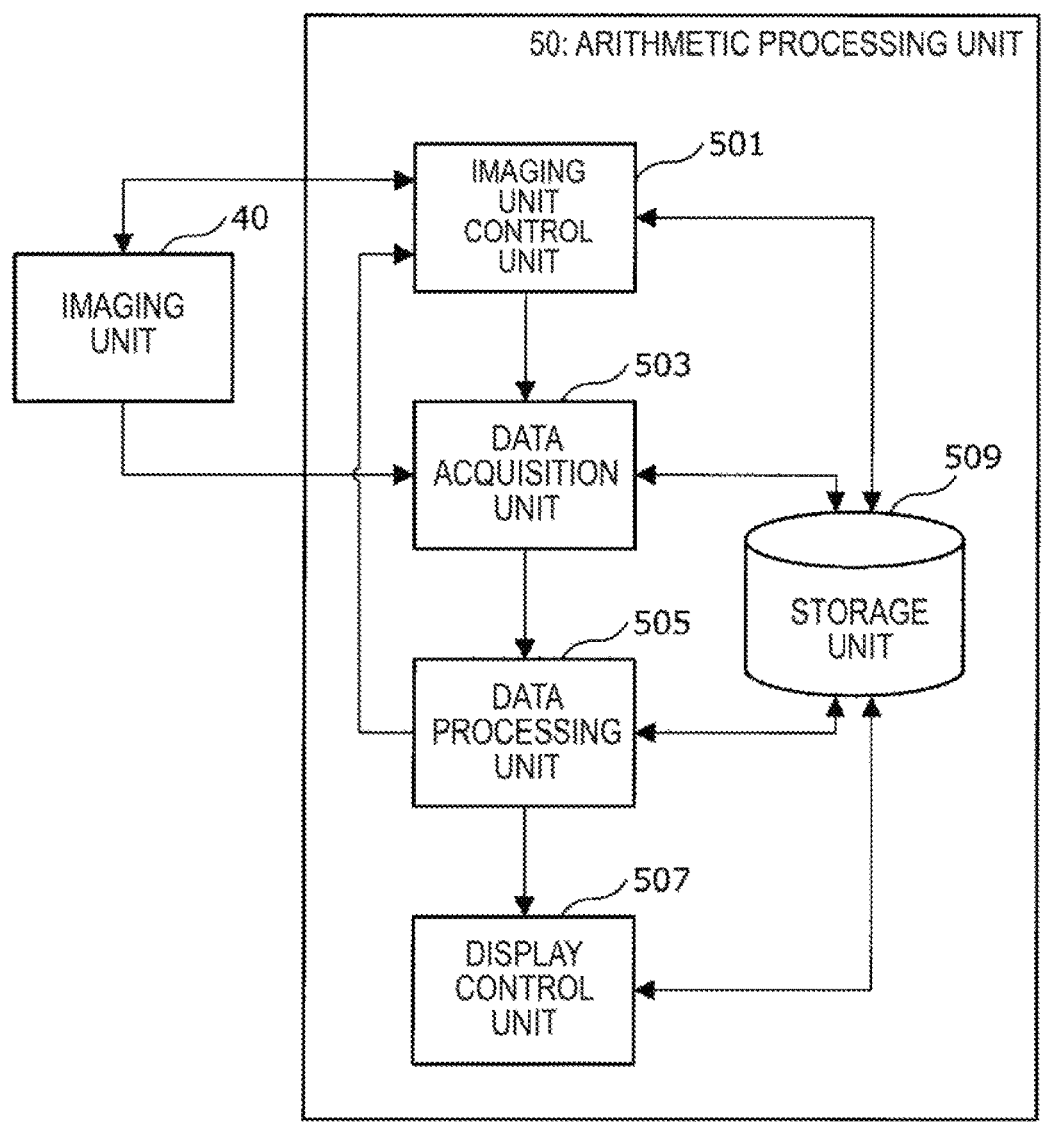
FIG. 19 is a block diagram showing an example of a configuration of an arithmetic processing unit according to the embodiment.
Figure 20:
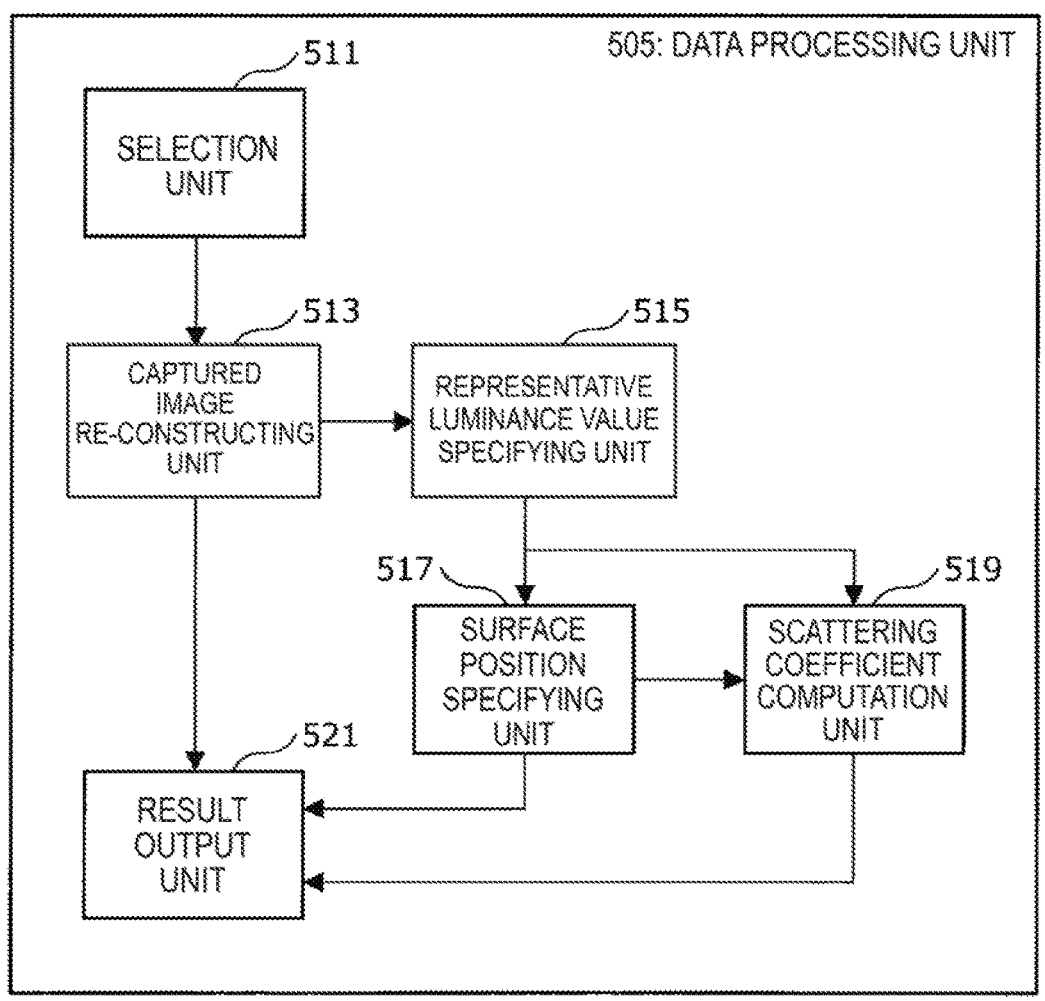
FIG. 20 is a block diagram showing an example of a configuration of a data processing unit according to the embodiment.
Figure 21:
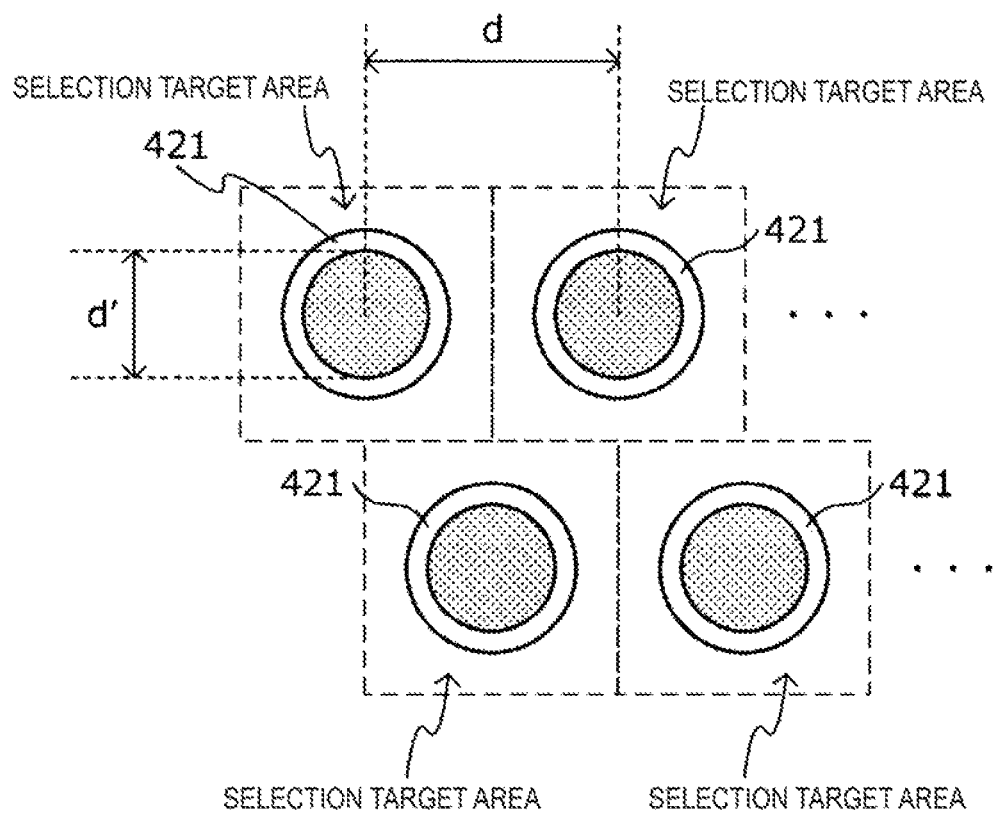
FIG. 21 is an illustrative diagram for describing a representative pixel value selection process of the data processing unit according to the embodiment.
Figure 22:
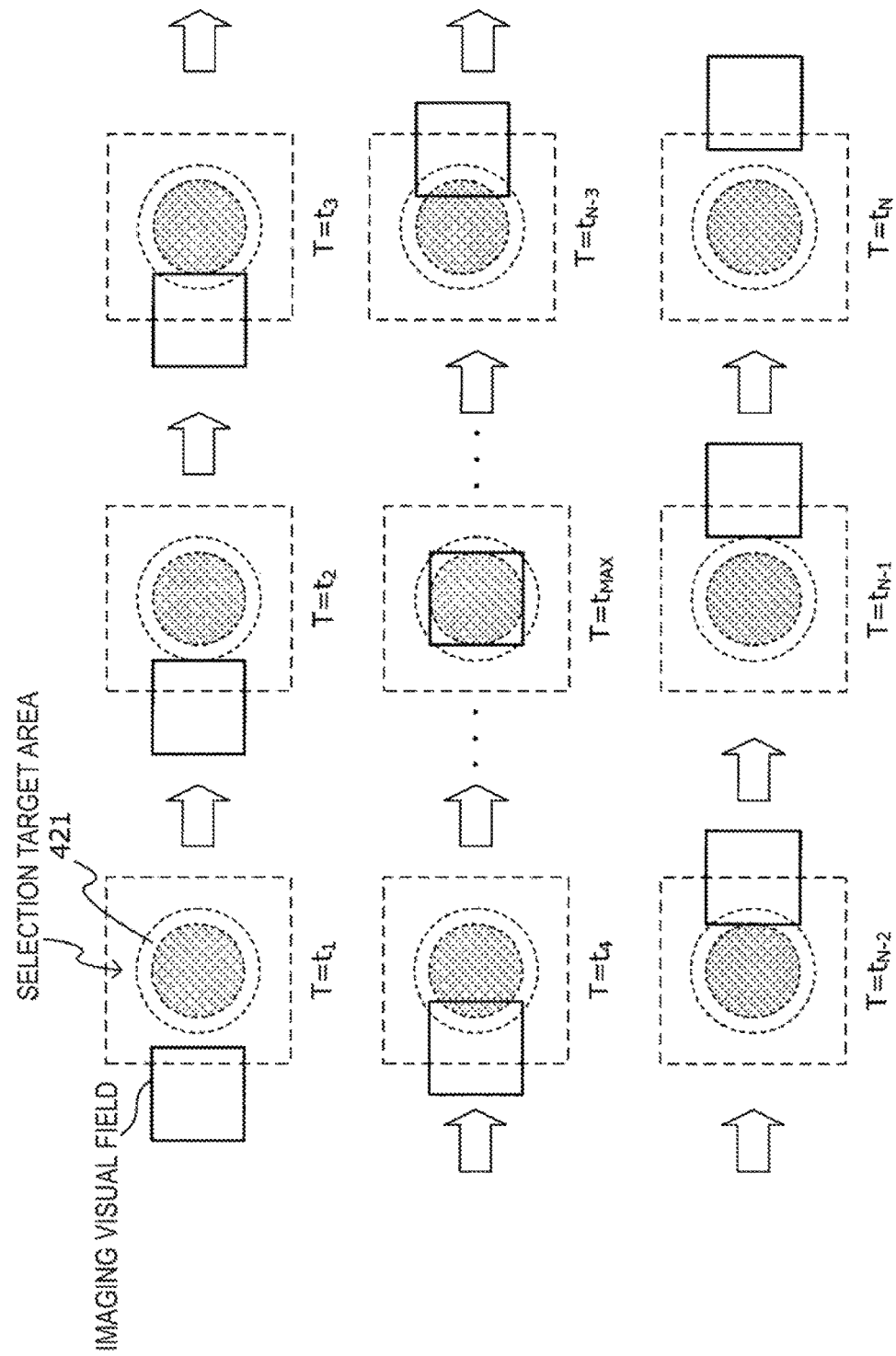
FIG. 22 is an illustrative diagram for describing a representative pixel value selection process of the data processing unit according to the embodiment.
Figure 23:
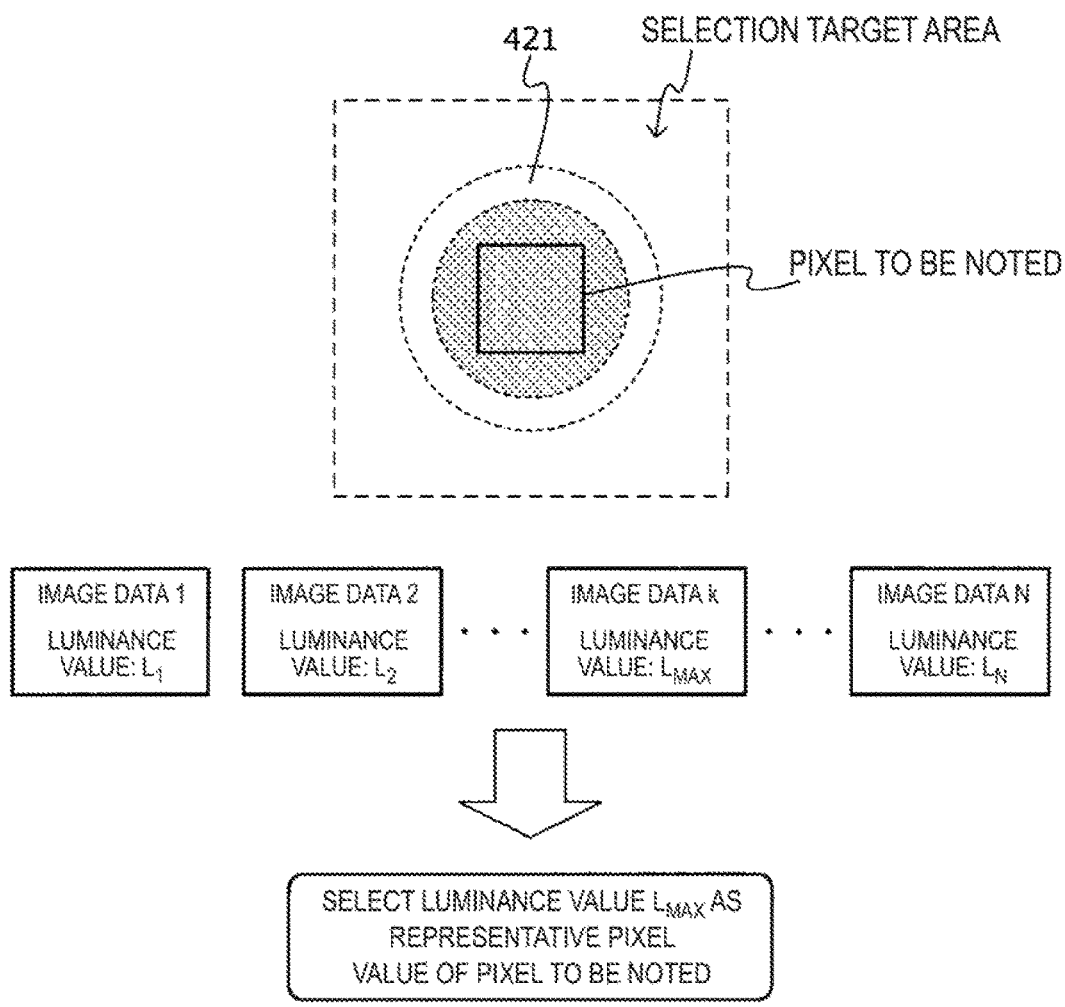
FIG. 23 is an illustrative diagram for describing a representative pixel value selection process of the data processing unit according to the embodiment.

FIG. 19 is a block diagram schematically showing a configuration of the arithmetic processing unit included in the image acquisition system according to the present embodiment. FIG. 20 is a block diagram showing an example of a configuration of a data processing unit according to the present embodiment. FIGS. 21 to 23 are illustrative diagrams for describing a representative pixel value selection process of the arithmetic processing unit according to the present embodiment.

The arithmetic processing unit 50 according to the present embodiment is a unit which controls operations of the imaging unit 40 and performs a predetermined arithmetic process on image data generated by the imaging unit 40, and thereby generates a plurality of fluorescence images each corresponding to thickness positions of the measurement subject S.

The arithmetic processing unit 50 mainly has an imaging unit control unit 501, a data acquisition unit 503, a data processing unit 505, a display control unit 507, and a storage unit 509 as schematically illustrated in FIG. 19.

The imaging unit control unit 501 is realized by, for example, a CPU, a ROM, a RAM, a communication device, and the like. The imaging unit control unit 501 transmits and receives various control signals to and from the light source, the optical elements, the scanning mechanism, and the like constituting the imaging unit 40 according to the present embodiment, and thereby generally manages various operations of the imaging unit 40. Accordingly, the light source of the imaging unit 40 emits excitation light at a predetermined timing, or an end face of the image guide fiber 403 is scanned on the basis of the above-described scanning methods. In addition, the light source, the optical elements, the scanning mechanism, and the like constituting the imaging unit 40 may also be able to perform various kinds of control while cooperating with each other via the imaging unit control unit 501. In addition, various kinds of control information to be used when the imaging unit control unit 501 controls the imaging unit 40 (e.g., information regarding an imaging position and the like) are output to the data acquisition unit 503, the data processing unit 505, and the like when necessary and are appropriately used in various processes performed in the processing units.

Furthermore, the imaging unit control unit 501 according to the present embodiment may control power of excitation light radiated toward the measurement subject S using information regarding a scattering coefficient of the measurement subject S computed by the data processing unit 505 to be described below.

The data acquisition unit 503 is realized by, for example, a CPU, a ROM, a RAM, a communication device, and the like. The data acquisition unit 503 acquires a plurality of pieces of image data generated by the imaging unit 40 on the basis of the above-described scanning methods from the imaging unit 40. The plurality of pieces of image data acquired by the data acquisition unit 503 are transmitted to the data processing unit 505 to be described below. In addition, the data acquisition unit 503 may associate the acquired plurality of pieces of image data with time information regarding a date, time and the like at which the image data was acquired, and may store the associated data in the storage unit 509 to be described below as hi story information.

The data processing unit 505 is realized by, for example, a CPU, a ROM, a RAM, and the like. The data processing unit 505 generates fluorescence images of the measurement subject S by performing various data processes on the plurality of images captured by the imaging unit 40 transmitted from the data acquisition unit 503, and specifies a position of a surface and the scattering coefficient of the measurement subject S further using the obtained fluorescence images. When the above-described various kinds of information are computed, the data processing unit 505 outputs the generated fluorescence images and the computed information regarding image information to the display control unit 507. Accordingly, the fluorescence images of the measurement subject S and the image information regarding the fluorescence images are output to a display unit (not illustrated) of the arithmetic processing unit 50 or any of a variety of computers and the like that can communicate with the arithmetic processing unit 50. In addition, the data processing unit 505 may output the obtained fluorescence images and image information to various recording media, various computers, and the like, or may output the obtained fluorescence images and image information to a paper medium or the like using an output device such as a printer. In addition, the data processing unit 505 may associate the fluorescence images of the measurement subject S and the image information regarding the fluorescence images with time information regarding a date, time, and the like at which the information was computed and store the associated data in the storage unit 509 as history information.

Note that a detailed configuration of the data processing unit 505 will be described below.

The display control unit 507 is realized by, for example, a CPU, a ROM, a RAM, an output device, and the like. The display control unit 507 performs display control to display the fluorescence images of the measurement subject S, the position of the surface of the measurement subject S, and various processing results including information regarding the scattering coefficient and the like of the measurement subject S transmitted from the data processing unit 505 on an output device such as a display provided in the arithmetic processing unit 50, an output device provided outside of the arithmetic processing unit 50, or the like. Accordingly, a user of the image acquisition system 30 can immediately ascertain various processing results with regard to the measurement subject S.

The storage unit 509 is realized by, for example, a RAM, a storage device, or the like provided in the arithmetic processing unit 50 according to the present embodiment. The storage unit 509 appropriately records various parameters and process developments that need to be saved by the arithmetic processing unit 50 according to the present embodiment to perform any process or various databases, programs, and the like. The storage unit 509 enables the imaging unit control unit 501, the data acquisition unit 503, the data processing unit 505, the display control unit 507, and the like to freely perform data read and write processes.

[Regarding Configuration of Data Processing Unit 505]

Next, a configuration of the data processing unit 505 provided in the arithmetic processing unit 50 according to the present embodiment will be described in detail with reference to FIGS. 20 to 23.

The data processing unit 505 according to the present embodiment is provided with a selection unit 511, a captured image re-constructing unit 513, a representative luminance value specifying unit 515, a surface position specifying unit 517, a scattering coefficient computation unit 519, and a result output unit 521 as illustrated in FIG. 20.

The selection unit 511 is realized by, for example, a CPU, a ROM, a RAM, and the like. The selection unit 511 selects, for each of a plurality of pixels constituting an optical fiber element wire-corresponding area, a pixel value that is maximum luminance of a plurality of pieces of image data transmitted from the data acquisition unit 503 as a representative pixel value of the pixel. A process of selecting a representative pixel value executed by the selection unit 511 will be described in detail below with reference to FIGS. 21 to 23.

The image guide fiber 403 is formed by bundling a plurality of optical fiber element wires 421, an optical fiber element wire-corresponding area, which is an area corresponding to one of the optical fiber element wires 421, can be virtually defined on the basis of the interval (the disposition pitch) d between adjacent optical fiber element wires and the core diameter d' of the optical fiber element wire 421 as schematically illustrated in FIG. 21. The selection unit 511 according to the present embodiment deals with the optical fiber element wire-corresponding area defined for each of the optical fiber element wires 421 as a selection target area in the process for selecting a representative pixel value as will be described in detail below.

By realizing the scanning methods shown in FIGS. 16A and 16B by the imaging unit 40, an imaging visual field of a detector provided in the imaging optical system 405 moves in a certain selection target area in accordance with the elapse of time as schematically illustrated in FIG. 22.

Here, in a multi-photon excitation process including a two-photon excitation process, as optical fiber element wires have a lower-order optical waveguide mode, luminance of generated fluorescence increases. In addition, as an imaging target area of an imaging subject at that time point is positioned closer to the center of a core, luminance of generated fluorescence increases. Thus, by acquiring images a plurality of times and selecting a highest fluorescence value, it is possible to selectively acquire information of the fluorescence generated through the multi-photon excitation process using excitation light that has reached the sample-side end face in the zero-order mode. Here, the highest fluorescence value is considered to be given in image data captured at a position corresponding to a time $T=t_{MAX}$ in FIG. 22.

Thus, the selection unit 511 refers to the luminance value at positions of a plurality of pieces of image data including a pixel to be noted for each of pixels constituting the selection target area and specifies the highest luminance value. Then, the selection unit 511 uses the specified highest luminance value as a representative pixel value of the pixel to be noted. As schematically illustrated in FIG. 23, when, for example, there are N pieces of image data 1 to N for pixels to be noted, the N pieces of image data are searched transversally, and image data that gives a highest luminance value $L_{MAX}$ is used as image data of the pixels to be noted. In the case of FIG. 23, image data k is used as image data that gives a representative pixel value of the pixels to be noted.

The selection unit 511 executes the process for selecting a representative pixel value described above for all selection target areas (i.e., all optical fiber element wire-corresponding areas).

Here, the image data that gives the maximum luminance value is considered to be superimposed with noise accompanying the luminance value, and thus the selection unit 511 may select image data that gives a luminance value approximate to the highest luminance value instead of image data giving the highest luminance value.

Note that, although the case in which the selection unit 511 transversely searches the plurality of pieces of generated image data and selects image data that gives the highest luminance value has been described in the above description, a specific highest luminance value can also be specified using the following method. That is, the selection unit 511 may specify the highest luminance value by comparing data of neighboring pixels and performing a filtering process of selecting a maximum luminance value of an optical fiber element wire-corresponding area. As such a filtering process, for example, an ordinary filtering for an area of 10 pixels×10 pixels or the like can be exemplified. Using the filtering process, the highest luminance value of pixels to be noted can be more quickly and easily searched for.

When a representative pixel value is selected using the above-described method, the selection unit 511 outputs information regarding the selected representative pixel value to the captured image re-constructing unit 513.

The captured image re-constructing unit 513 is realized by, for example, a CPU, a ROM, a RAM, and the like. The captured image re-constructing unit 513 re-constructs captured images of the imaging subject S using the selected representative pixel value. Accordingly, a fluorescence image of the measurement subject S expressing a state of fluorescence generated through the multi-photon excitation process can be generated.

Note that the captured image re-constructing unit 513 may cause a blur filter represented by a Gaussian filter to act on the generated fluorescence image of the measurement subject S. Accordingly, a fluorescence image in which the selected representative pixel value is more smoothly connected can be obtained.

Furthermore, the captured image re-constructing unit 513 may execute known post-processing other than the above processes on the generated fluorescence image.

The captured image re-constructing unit 513 outputs the fluorescence image generated as described above to the representative luminance value specifying unit 515 and the result output unit 521.

The representative luminance value specifying unit 515, the surface position specifying unit 517, and the scattering coefficient computation unit 519 each have similar configurations and exhibit similar effects to those of the representative luminance value specifying unit 111, the surface position specifying unit 113, and the scattering coefficient computation unit 115 provided in the information processing device 10 according to the first embodiment of the present disclosure, and thus detailed description thereof will be omitted below.

The result output unit 521 is realized by, for example, a CPU, a ROM, a RAM, a communication device, and the like. The result output unit 521 outputs the fluorescence image generated by the captured image re-constructing unit 513, information regarding a position of a surface of the measurement subject S specified by the surface position specifying unit 517, or information regarding the scattering coefficient $R_S$ of the measurement subject S computed by the scattering coefficient computation unit 519.

So far, examples of the functions of the arithmetic processing unit 50 according to the present embodiment have been introduced. The respective constituent elements may be configured using universal members and circuits, or may be configured using hardware specialized for the functions of the constituent elements. In addition, all of the functions of the constituent elements may be fulfilled by a CPU and the like. Thus, a configuration to be used can be appropriately changed in accordance with a technical level of any occasion at which the present embodiment is implemented.

Note that a computer program for realizing each function of the arithmetic processing unit according to the present embodiment described above can be produced and installed in personal computers and the like. In addition, a computer-readable recording medium on which the computer program is stored can also be provided. The recording medium is, for example, a magnetic disk, an optical disc, a magneto-optical disc, a flash memory, or the like. Furthermore, the computer program may be distributed through, for example, a network, without using a recording medium.

(Hardware Configuration)

Figure 24:
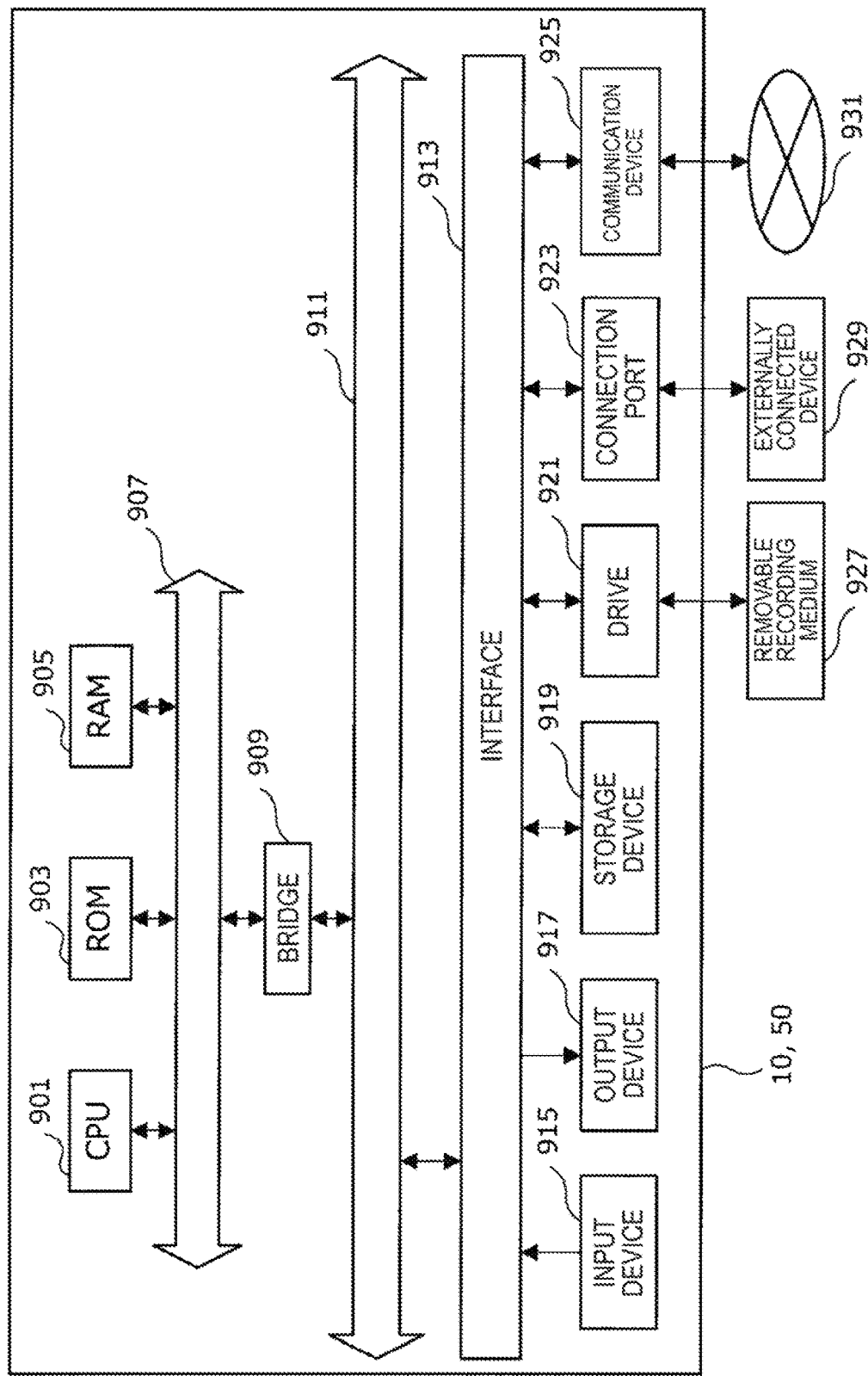
FIG. 24 is a block diagram showing an example of a hardware configuration of an information processing device and an arithmetic operation processing unit according to an embodiment of the present disclosure.

Next, the hardware configuration of the information processing device 10 and the arithmetic processing unit 50 according to the embodiment of the present disclosure will be described in detail with reference to FIG. 24. FIG. 24 is a block diagram for illustrating the hardware configuration of the information processing device 10 and the arithmetic processing unit 50 according to the embodiment of the present disclosure.

The information processing device 10 and the arithmetic processing unit 50 mainly include a CPU 901, a ROM 903, and a RAM 905. Furthermore, the arithmetic processing device 20 also includes a host bus 907, a bridge 909, an external bus 911, an interface 913, an input device 915, an output device 917, a storage device 919, a drive 921, a connection port 923, and a communication device 925.

The CPU 901 serves as an arithmetic processing device and a control device, and controls the overall operation or a part of the operation of the information processing device 10 and the arithmetic processing unit 50 according to various programs recorded in the ROM 903, the RAM 905, the storage device 919, or a removable recording medium 927. The ROM 903 stores programs, operation parameters, and the like used by the CPU 901. The RAM 905 primarily stores programs used in execution of the CPU 901 and parameters and the like varying as appropriate during the execution. These are connected with each other via the host bus 907 configured from an internal bus such as a CPU bus or the like.

The host bus 907 is connected to the external bus 911 such as a PCI (Peripheral Component Interconnect/Interface) bus via the bridge 909.

The input device 915 is an operation means operated by a user, such as a mouse, a keyboard, a touch panel, buttons, a switch and a lever. Also, the input device 915 may be a remote control means (a so-called remote control) using, for example, infrared light or other radio waves, or may be an externally connected device 929 such as a mobile phone or a PDA conforming to the operation of the information processing device 10 and the arithmetic processing unit 50. Furthermore, the input device 915 generates an input signal based on, for example, information which is input by a user with the above operation means, and is configured from an input control circuit for outputting the input signal to the CPU 901. The user can input various data to the information processing device 10 and the arithmetic processing unit 50 and can instruct the information processing device 10 and the arithmetic processing unit 50 to perform processing by operating this input device 915.

The output device 917 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 917 outputs a result obtained by various processings performed by the information processing device 10 and the arithmetic processing unit 50. More specifically, the display device displays, in the form of texts or images, a result obtained by various processes performed by the information processing device 10 and the arithmetic processing unit 50. On the other hand, the audio output device converts an audio signal such as reproduced audio data and sound data into an analog signal, and outputs the analog signal.

The storage device 919 is a device for storing data configured as an example of a storage unit of the information processing device 10 and the arithmetic processing unit 50 and is used to store data. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, various data, and sound signal data, image signal data, or the like, obtained externally.

The drive 921 is a reader/writer for recording medium, and is embedded in the information processing device 10 and the arithmetic processing unit 50 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray (registered trademark) medium. The removable recording medium 927 may be a CompactFlash (CF; registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing devices to directly connect to the information processing device 10 and the arithmetic processing unit 50. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (High-Definition Multimedia Interface) port, and the like. By the externally connected device 929 connecting to this connection port 923, the information processing device 10 and the arithmetic processing unit 50 directly obtains sound signal data, image signal data, or the like, from the externally connected device 929 and provides sound signal data, image signal data, or the like, to the externally connected device 929.

The communication device 925 is a communication interface configured from, for example, a communication device for connecting to a communication network 931. The communication device 925 is, for example, a wired or wireless LAN (Local Area Network), Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol such as TCP/IP on the Internet and with other communication devices, for example. The communication network 931 connected to the communication device 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the information processing device 10 and the arithmetic processing unit 50 according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
An information processing device including:
a representative luminance value specifying unit configured to, when luminance values constituting a plurality of fluorescence images of a measurement subject captured while a position of the measurement subject in a thickness direction is changed are sequentially rearranged from a highest luminance value on the basis of the fluorescence images for each of the fluorescence images corresponding to respective thickness positions, extract a luminance value ranked at a predetermined position from the highest luminance value and set the extracted luminance value as a representative luminance value of the fluorescence image at the thickness position to be noted; and
a surface position specifying unit configured to use the representative luminance value for each of the fluorescence images and set the thickness position corresponding to the fluorescence image that gives the maximum representative luminance value as a position corresponding to a surface of the measurement subject.

(2)
The information processing device according to (1), wherein the predetermined ranked position is a position included in a range of a top 0.5% to 5% of the number of all pixels constituting one fluorescence image with reference to the highest luminance value.

(3)

The information processing device according to (1) or (2), further including:

a scattering coefficient computation unit configured to compute a scattering coefficient of the measurement subject from a degree of change of the representative luminance value in the thickness direction using the representative luminance value for each of the fluorescence images.

(4)

The information processing device according to (3), wherein the scattering coefficient computation unit computes the scattering coefficient using the representative luminance values at three thickness positions having equal intervals on the basis of the representative luminance values of the fluorescence images corresponding to deeper parts than the position corresponding to the surface of the measurement subject.

(5)

The information processing device according to (4), wherein the fluorescence image is obtained by capturing fluorescence generated when the measurement subject is excited with N (N is an integer that is greater than or equal to 1) photons, and when the representative luminance value at a thickness position $x_i$ (i=1, 2, and 3) is denoted by $A_i$ (i=1, 2, and 3), and an interval between the two adjacent thickness positions is denoted by dx, the scattering coefficient computation unit computes a scattering coefficient R on the basis of the following formula 1.

(6)

An image acquisition system including:

an imaging unit configured to generate a plurality of pieces of image data for fluorescence generated from a measurement subject by radiating excitation light toward the measurement subject and imaging the fluorescence of the measurement subject while changing a position of the measurement subject in a thickness direction; and an arithmetic processing unit configured to generate a plurality of fluorescence images corresponding to respective thickness positions by controlling the imaging unit and performing data processing on each of the plurality of pieces of image data generated by the imaging unit, wherein the imaging unit includes a light source optical system configured to guide excitation light for exciting the measurement subject with two or more photons to generate fluorescence toward the measurement subject, an image guide fiber which is formed by bundling a plurality of multimode optical fiber element wires and is configured to transmit the excitation light incident on one end to the measurement subject from the light source optical system and transmit an image of the measurement subject formed on the other end using the fluorescence generated from the measurement subject to the one end, and an imaging optical system configured to scan the image of the measurement subject transmitted to the one end of the image guide fiber at a scanning pitch that is narrower than a size of a core of each of the plurality of optical fiber element wires to perform imaging such that at least a part of an optical fiber element wire-corresponding area which corresponds to each of the optical fiber element wires is included in a plurality of images, and generate a plurality of pieces of image data of the measurement subject, and the arithmetic processing unit includes a selection unit configured to select, for each of a plurality of pixels constituting the optical fiber element wire-corresponding area, a pixel value that has maximum luminance among the plurality of pieces of image data as a representative pixel value of the pixel, a captured image re-constructing unit configured to re-construct the captured image of the measurement subject using the selected representative pixel value and generate the fluorescence image, a representative luminance value specifying unit configured to, when luminance values constituting the plurality of fluorescence images captured while the position of the measurement subject in the thickness direction is changed are sequentially rearranged from a highest luminance value on the basis of the fluorescence images for each of the fluorescence images corresponding to respective thickness positions, extract a luminance value ranked at a predetermined position from the highest luminance value and set the extracted luminance value as a representative luminance value of the fluorescence image at the thickness position to be noted, and a surface position specifying unit configured to use the representative luminance value for each of the fluorescence images and set the thickness position corresponding to the fluorescence image that gives the maximum representative luminance value as a position corresponding to a surface of the measurement subject.

(7)

The image acquisition system according to (6), wherein an optical component for a hologram which can simultaneously acquire fluorescence from different thickness positions of the measurement subject is provided at a measurement subject-side end of the image guide fiber.

(8)

An information processing method including:

extracting, when luminance values constituting a plurality of fluorescence images of a measurement subject captured while a position of the measurement subject in a thickness direction is changed are sequentially rearranged from a highest luminance value on the basis of the fluorescence images for each of the fluorescence images corresponding to respective thickness positions, a luminance value ranked at a predetermined position from the highest luminance value and setting the extracted luminance value as a representative luminance value of the fluorescence image to be noted; and using the representative luminance value for each of the fluorescence images and setting the thickness position corresponding to the fluorescence image that gives the maximum representative luminance value as a position corresponding to a surface of the measurement subject.

(9)

An image information acquisition method including:

guiding excitation light for exciting a measurement subject with two or more photons to generate fluorescence toward the measurement subject;

transmitting the excitation light incident on one end of an image guide fiber which is formed by bundling a plurality of multimode optical fiber element wires toward the measurement subject using the image guide fiber, and transmitting an image of the measurement subject formed on the other end using the fluorescence generated from the measurement subject to the one end while changing a position of the measurement subject in a thickness direction;

scanning the image of the measurement subject transmitted to the one end of the image guide fiber at a scanning pitch that is narrower than a size of a core of each of the plurality of optical fiber element wires to perform imaging such that at least a part of an optical fiber element wire-corresponding area which corresponds to each of the optical fiber element wires is included in a plurality of images, and generating a plurality of pieces of image data of the measurement subject;

selecting, for each of a plurality of pixels constituting the optical fiber element wire-corresponding area, a pixel value that has maximum luminance among the plurality of pieces of image data as a representative pixel value of the pixel;

re-constructing the captured image of the measurement subject using the selected representative pixel value and generating a fluorescence image;

extracting, when luminance values constituting a plurality of fluorescence images captured while the position of the measurement subject in the thickness direction is changed are sequentially rearranged from a highest luminance value on the basis of the fluorescence images for each of the fluorescence images corresponding to respective thickness positions, a luminance value ranked at a predetermined position from the highest luminance value and setting the extracted luminance value as a representative luminance value of the fluorescence image at the thickness position to be noted; and using the representative luminance value for each of the fluorescence images and setting the thickness position corresponding to the fluorescence image that gives the maximum representative luminance value as a position corresponding to a surface of the measurement subject.

(10)

A program causing a computer to realize:

a representative luminance value specifying function of extracting, when luminance values constituting a plurality of fluorescence images of a measurement subject captured while a position of the measurement subject in a thickness direction is changed are sequentially rearranged from a highest luminance value on the basis of the fluorescence images for each of the fluorescence images corresponding to thickness positions, a luminance value ranked at a predetermined position from the highest luminance value and setting the extracted luminance value as a representative luminance value of the fluorescence image to be noted; and a surface position specifying function of using the representative luminance value for each of the fluorescence images and setting the thickness position corresponding to the fluorescence image that gives the maximum representative luminance value as a position corresponding to a surface of the measurement subject.

[Math. 3]

$$S = -\frac{1}{N \cdot dx} \cdot \ln\left(\frac{A_1 - A_2}{A_2 - A_3}\right) \qquad \text{(Formula 1)}$$

REFERENCE SIGNS LIST 10 information processing device
20, 40 imaging unit
30 image acquisition system
50 arithmetic processing unit
101, 503 data acquisition unit
103 image information computation unit
105, 507 display control unit
107, 509 storage unit
111, 515 representative luminance value specifying unit
113, 517 surface position specifying unit
115, 519 scattering coefficient computation unit
117, 521 result output unit
401 light source optical system
403 image guide fiber
405 imaging optical system
421 optical fiber element wire
423 core
425 cladding
501 imaging unit control unit
505 data processing unit
511 selection unit
513 captured image re-constructing unit

The invention claimed is:

1. An information processing device, comprising:
    a representative luminance value specifying unit configured to, when luminance values constituting a plurality of fluorescence images of a measurement subject captured while a position of the measurement subject in a thickness direction is changed are sequentially rearranged from a highest luminance value based on the plurality of fluorescence images corresponding to respective thickness positions, extract a luminance value ranked at a predetermined position from the highest luminance value and set the extracted luminance value as a representative luminance value of a fluorescence image at a thickness position to be noted; and
    a surface position specifying unit configured to use the representative luminance value for each of the plurality of fluorescence images and set the thickness position corresponding to the fluorescence image that gives a maximum representative luminance value as a position corresponding to a surface of the measurement subject.

2. The information processing device according to claim 1, wherein the predetermined position is a position included in a range of a top 0.5% to 5% of a number of all pixels constituting one fluorescence image with reference to the highest luminance value.

3. The information processing device according to claim 1, further comprising:
    a scattering coefficient computation unit configured to compute a scattering coefficient of the measurement subject from a degree of change of the representative luminance value in the thickness direction using the representative luminance value for each of the plurality of fluorescence images.

4. The information processing device according to claim 3, wherein the scattering coefficient computation unit computes the scattering coefficient using representative luminance values at three thickness positions having equal intervals based on the representative luminance values of fluorescence images corresponding to deeper parts than the position corresponding to the surface of the measurement subject.

5. The information processing device according to claim 4,
    wherein the fluorescence image is obtained by capture of fluorescence generated when the measurement subject is excited with N (N is an integer that is greater than or equal to 1) photons, and
    when the representative luminance value at a thickness position $x_i$ (i=1, 2, and 3) is denoted by Ai (i=1, 2, and 3), and an interval between two adjacent thickness positions is denoted by dx, the scattering coefficient computation unit computes a scattering coefficient Rs based on the following formula 1

[Math. 1]

$$R_s = -\frac{1}{N \cdot dx} \cdot \ln\left(\frac{A_1 - A_2}{A_2 - A_3}\right).$$ (Formula 1)

6. An image acquisition system, comprising:
an imaging unit configured to generate a plurality of pieces of image data for fluorescence generated from a measurement subject by radiation of an excitation light towards the measurement subject and imaging the fluorescence of the measurement subject while a position of the measurement subject is changed in a thickness direction; and
an arithmetic processing unit configured to generate a plurality of fluorescence images corresponding to respective thickness positions by controlling the imaging unit and perform data processing on each of the plurality of pieces of image data generated by the imaging unit,
wherein the imaging unit includes:
  a light source optical system configured to guide the excitation light for excitation of the measurement subject with at least two photons to generate fluorescence toward the measurement subject,
  an image guide fiber which is formed by bundling a plurality of multimode optical fiber element wires and is configured to transmit the excitation light incident on one end to the measurement subject from the light source optical system and transmit an image of the measurement subject formed on an other end using the fluorescence generated from the measurement subject to the one end, and
  an imaging optical system configured to scan the image of the measurement subject transmitted to the one end of the image guide fiber at a scanning pitch that is narrower than a size of a core of each of the plurality of multimode optical fiber element wires to perform imaging such that at least a part of an optical fiber element wire-corresponding area which corresponds to each of the plurality of multimode optical fiber element wires is included in a plurality of images, and generate the plurality of pieces of image data of the measurement subject, and
the arithmetic processing unit includes:
  a selection unit configured to select, for each of a plurality of pixels constituting the optical fiber element wire-corresponding area, a pixel value that has maximum luminance among the plurality of pieces of image data as a representative pixel value of a pixel,
  a captured image re-constructing unit configured to re-construct a captured image of the measurement subject using the selected representative pixel value and generate a fluorescence image,
  a representative luminance value specifying unit configured to, when luminance values constituting the plurality of fluorescence images captured while the position of the measurement subject in the thickness direction is changed are sequentially rearranged from a highest luminance value based on the plurality of fluorescence images corresponding to respective thickness positions, extract a luminance value ranked at a predetermined position from the highest luminance value and set the extracted luminance value as a representative luminance value of the fluorescence image at a thickness position to be noted, and
  a surface position specifying unit configured to use the representative luminance value for each of the plurality of fluorescence images and set the thickness position corresponding to the fluorescence image that gives a maximum representative luminance value as a position corresponding to a surface of the measurement subject.

7. The image acquisition system according to claim 6, wherein an optical component for a hologram which can simultaneously acquire the fluorescence from different thickness positions of the measurement subject is provided at a measurement subject-side end of the image guide fiber.

8. An information processing method, comprising:
extracting, when luminance values constituting a plurality of fluorescence images of a measurement subject captured while a position of the measurement subject in a thickness direction is changed are sequentially rearranged from a highest luminance value based on the plurality of fluorescence images corresponding to respective thickness positions, a luminance value ranked at a predetermined position from the highest luminance value and setting the extracted luminance value as a representative luminance value of a fluorescence image to be noted; and
using the representative luminance value for each of the plurality of fluorescence images and setting a thickness position corresponding to the fluorescence image that gives a maximum representative luminance value as a position corresponding to a surface of the measurement subject.

9. An image information acquisition method, comprising:
guiding an excitation light for exciting a measurement subject with at least two photons to generate fluorescence toward the measurement subject;
transmitting the excitation light incident on one end of an image guide fiber which is formed by bundling a plurality of multimode optical fiber element wires toward the measurement subject using the image guide fiber, and transmitting an image of the measurement subject formed on an other end using the fluorescence generated from the measurement subject to the one end while changing a position of the measurement subject in a thickness direction;
scanning the image of the measurement subject transmitted to the one end of the image guide fiber at a scanning pitch that is narrower than a size of a core of each of the plurality of multimode optical fiber element wires to perform imaging such that at least a part of an optical fiber element wire-corresponding area which corresponds to each of the plurality of multimode optical fiber element wires is included in a plurality of images, and generating a plurality of pieces of image data of the measurement subject;
selecting, for each of a plurality of pixels constituting the optical fiber element wire- corresponding area, a pixel value that has maximum luminance among the plurality of pieces of image data as a representative pixel value of a pixel;
re-constructing a captured image of the measurement subject using the selected representative pixel value and generating a fluorescence image;
extracting, when luminance values constituting a plurality of fluorescence images captured while the position of the measurement subject in the thickness direction is changed are sequentially rearranged from a highest luminance value based on the plurality of fluorescence images corresponding to respective thickness positions, a luminance value ranked at a predetermined position from the highest luminance value and setting the extracted luminance value as a representative luminance value of the fluorescence image at a thickness position to be noted; and using the representative luminance value for each of the plurality of fluorescence images and setting the thickness position corresponding to the fluorescence image that gives a maximum representative luminance value as a position corresponding to a surface of the measurement subject.

* * * * *